United States Patent [19]

Brown et al.

[11] Patent Number: 5,714,496

[45] Date of Patent: *Feb. 3, 1998

[54] QUINUCLIDINE DERIVATIVES AS SQUALENE SYNTHASE INHIBITORS

[75] Inventors: George Robert Brown, Wilmslow; Keith Blakeney Mallion, Knutsford; Paul Robert Owen Whittamore, Macclesfield; David Robert Brittain, Rochdale, all of Great Britain

[73] Assignee: Zeneca Limited, London, United Kingdom

[*] Notice: The term of this patent shall not extend beyond the expiration date of Pat. No. 5,554,613.

[21] Appl. No.: 392,928

[22] PCT Filed: Aug. 25, 1993

[86] PCT No.: PCT/GB93/01802

§ 371 Date: Feb. 28, 1995

§ 102(e) Date: Feb. 28, 1995

[87] PCT Pub. No.: WO94/05660

PCT Pub. Date: Mar. 17, 1994

[30] Foreign Application Priority Data

Aug. 28, 1992 [GB] United Kingdom ............ 9218334

[51] Int. Cl.[6] .................. A61K 31/435; C07D 453/02
[52] U.S. Cl. ...................... 514/305; 546/133; 546/137
[58] Field of Search .......................... 546/133, 137; 514/305

[56] References Cited

U.S. PATENT DOCUMENTS

| | | | |
|---|---|---|---|
| 3,405,134 | 10/1968 | Judd | 260/294.3 |
| 3,534,053 | 10/1970 | Sallay et al. | 260/294.7 |
| 3,586,694 | 6/1971 | Shen et al. | 260/309.2 |
| 3,655,675 | 4/1972 | Carabateas | 260/293.74 |
| 3,679,690 | 7/1972 | Carabateas | 260/295.5 |
| 3,725,410 | 4/1973 | Potoski et al. | 260/268 BC |
| 3,763,168 | 10/1973 | Carabateas | 260/293.53 |
| 3,857,848 | 12/1974 | Mauvernay et al. | 260/293.53 |
| 4,038,402 | 7/1977 | Kaminka et al. | 424/267 |
| 4,599,344 | 7/1986 | Morgan | 514/305 |
| 5,135,935 | 8/1992 | Alberts et al. | 514/305 |
| 5,242,914 | 9/1993 | Kawamoto et al. | 514/210 |
| 5,286,864 | 2/1994 | Walther et al. | 546/137 |
| 5,385,912 | 1/1995 | Neuenschwander et al. | 514/305 |
| 5,554,613 | 9/1996 | Mallion | 514/253 |

FOREIGN PATENT DOCUMENTS

| | | |
|---|---|---|
| 77130/91 | 11/1991 | Australia. |
| 1014958 | 8/1977 | Canada. |
| 0 307 142 | 3/1989 | European Pat. Off.. |
| 0 316 718 | 5/1989 | European Pat. Off.. |
| 0 322 182 | 6/1989 | European Pat. Off.. |
| 0 328 200 | 8/1989 | European Pat. Off.. |
| 0 330 826 | 9/1989 | European Pat. Off.. |
| 0 337 637 | 10/1989 | European Pat. Off.. |
| 0 370 415 | 5/1990 | European Pat. Off.. |
| 0 412 797 | 2/1991 | European Pat. Off.. |
| 0 458 214 | 11/1991 | European Pat. Off.. |
| 0 497 415 | 8/1992 | European Pat. Off.. |
| 2 323 303 | 12/1973 | Germany. |
| 25 02 916 | 11/1975 | Germany. |
| 41 16 582 | 11/1991 | Germany. |
| 1 416 958 | 12/1975 | United Kingdom. |
| 2 169 292 | 7/1986 | United Kingdom. |
| 92 15579 | 9/1992 | WIPO. |
| 92/15579 | 9/1992 | WIPO. |
| 93 13096 | 7/1993 | WIPO. |
| 93/15073 | 8/1993 | WIPO. |
| 93/16048 | 8/1993 | WIPO. |

OTHER PUBLICATIONS

Saudman RA and McHugh WC (1977), 66(6) 890–1.

March J. in 'Advanced Organic Chemistry' Second Edition (1977) p. 434 McGraw Hill, N.Y.

Warawa et al. Quinuclidine Chemistry.2.[1]Synthesis and Antiinflammatory Properties of 2–Substituted Benzhydryl–3–quinuclidinols, J. Med. Chem. 17(5), (1974), 497–501.

Sterling et al, quaternary and Tertiary Quinuclidine Derivatives as Inhibitors of Choline Uptake, J. Pharm. Sciences, 80(8), (1991), 785–789.

Saunders et al, Novel Quinuclidine–Based Ligands for the Muscarinic Cholinergic Receptor, J. Med. Chem. 33(4), (1990), 1128–1137.

(List continued on next page.)

Primary Examiner—C. Warren Ivy
Assistant Examiner—Evelyn Huang
Attorney, Agent, or Firm—Cushman Darby & Cushman Intellectual Property Group of Pillsbury Madison & Sutro LLP

[57] ABSTRACT

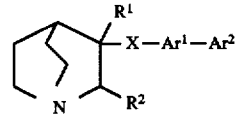

Compounds of formula (I) and their pharmaceutically acceptable salts in which $R^1$ is hydrogen or hydroxy; $R^2$ is hydrogen; or $R^1$ and $R^2$ are joined together so that $CR^1\text{–}CR^2$ is a double bond; X is selected from $-CH_2CH_2-$, $-CH=CH-$, $-C\equiv C-$, $-CH_2O-$, $-CH_2NH-$, $-NHCH_2-$, $-CH_2CO-$, $-COCH_2-$, $-CH_2S-$ and $-SCH_2-$; $Ar^1$ is a phenylene moiety; $Ar^2$ is a heteroaryl moiety; and wherein one or both of $Ar^1$ and $Ar^2$ may optionally bear one or more substituents independently selected from halogeno, hydroxy, amino, nitro, cyano, carboxy, carbamoyl, alkyl, alkenyl, alkynyl, alkoxy, alkylamino, di-alkylamino, N-alkylcarbamoyl, di-N,N-alkylcarbamoyl, alkoxycarbonyl, alkylthio, alkylsulphinyl, alkylsulphonyl, halogeno-alkyl, carboxyalkyl and alkanoylamino; provided that when $R^1$ is hydroxy, X is not selected from $-NHCH_2-$ and $-SCH_2-$; are inhibitors of squalene synthase and hence useful in treating medical conditions in which a lowering of cholesterol is beneficial, such as hypercholesterolemia and atherosclerosis. Processes for preparing these derivatives, pharmaceutical compositions containing them are also described together with their use in medicine.

12 Claims, No Drawings

OTHER PUBLICATIONS

Turchin et al, Stereochemistry of Quinuclidines Containing a Substituent with Aryl (Heteroaryl) Nuclei at Position Three Khimiko–farmatsevticheskii Zhurnal, 1986, vol. 20, pp. 65–72.

Bondarenko et al, Khim. Farm, 12(11), 1978, pp. 56–60. Khim, Farm, 7(8), 1973, 20–24.

Ricciardi et al, Facile Synthesis of Styrylquinuclidines, Heterocycles, 24, (1986), pp. 971–977.

Khim. Geterosikl Soedin, 3, (1983), 381–385.

Mikhlina et al, Synthesis and Properties of (3–Quinuclidyl-)diarylcarbinols, Khim. Geterosikl Soedin, 7,1976;776–780.

Sekine et al., Effect of Sulfur Containing Purine Nucleosides on Immunological Reaction in Mice, Japan. J. Exp. Med., 1973, vol. 43, 5, pp. 369–375.

DeVito et al., Synthesis and Pharmacological Evaluation of Some Novel 13–[N,N]dialkylamino–alkyl]benzo[g][2]benzopyrano[43–b]indol–5[13H]ones, Med. Chem. Res. 1(1), (1991), pp. 47–51.

Ermakov et al, Application of Mass Spectrometry in Structural and Stereochemical Investigations . . . , Khim. Geterosikl Soedin, 10, (1975), 1376–1383.

Mikhlina et al., Stereochemistry of Benzo[b]Quinuclidines . . . , Khim. Geterosikl Soedin, 6, (1973), pp. 839–843.

Fleet et al., Complex Quinuclidines (1–Azabicyclo[2.2.2] octanes) from Sugars: Synthesis of $1\alpha,3\alpha,4\alpha,5\alpha$)–Quinuclidine–3–,5–diol from D–Glucose, J. Chem. Soc. Perkin. Trans. 1(5), (1989), 1067–1068.

QUINUCLIDINE DERIVATIVES AS SQUALENE SYNTHASE INHIBITORS

This application is the national phase of PCT/GB93/01802, filed Aug. 24, 1993.

FIELD OF THE INVENTION

This invention concerns heterocyclic compounds which are useful in inhibiting squalene synthase, processes for their preparation and pharmaceutical compositions containing them. The present invention is also concerned with methods of using such heterocyclic compounds in treating diseases and medical conditions where inhibition of squalene synthase is desirable, for example in treating diseases or medical conditions such as hypercholesterolemia and atherosclerosis.

BACKGROUND TO INVENTION

Several different classes of compounds have been reported to possess the capability of being able to lower cholesterol levels in blood plasma. For example agents which inhibit the enzyme HMG CoA reductase, which is essential for the production of cholesterol, have been reported to reduce levels of serum cholesterol. Illustrative of this class of compounds is the HMG CoA reductase inhibitor known as lovastatin which is disclosed in U.S. Pat. No 4,231,938. Other agents which are reported to lower serum cholesterol include those which act by complexing with bile acids in the intestinal system and which are hence termed "bile acid sequestrants". It is believed that many of such agents act by sequestering bile acids within the intestinal tract. This results in a lowering of the levels of bile acid circulating in the enteroheptatic system and promoting replacement of bile acids by synthesis in the liver from cholesterol, which synthesis results in an upregulation of the heptatic LDL receptor and thus in a lowering of circulating blood cholesterol levels.

Squalene synthase (also referred to in the art as squalene synthetase) is a microsomal enzyme which catalyses the first committed step of cholesterol biosynthesis. Two molecules of farnesyl pyrophosphate (FFP) are condensed in the presence of the reduced form of nicotinamide adenine dinucleotide phosphate (NADPH) to form squalene. The inhibition of this committed step to cholesterol should leave unhindered biosynthetic pathways to ubiquinone, dolichol and isopentenyl t-RNA. Elevated cholesterol levels are known to be one of the main risk factors for ischaemic cardiovacsular disease. Thus, an agent which inhibits squalene synthase should be useful in treating diseases and medical conditions in which a reduction in the levels of cholesterol is desirable, for example hypercholesterolemia and atherosclerosis.

Thus far, the design of squalene synthase inhibitors has concentrated on the preparation of analogues of the substrate farnesyl pyrophosphate (FPP), and hence on compounds which contain phosphorus groups. For example, the preparation of phosphorous-containing squalene synthase inhibitors is reported in published European Patent Application No. 409,181; and the preparation of isoprenoid (phosphinylmethyl)phosphonates as inhibitors of squalene synthase is reported by Biller et al, J. Med. Chem., 1988, 31, 1869.

Recently, certain quinuclidine derivatives have been reported to inhibit squalene synthase (PCT Patent Application No. WO 92/15579, published 17 Sep. 1992).

DISCLOSURE OF INVENTION

The present invention is based on the discovery that certain heterocyclic compounds are inhibitors of squalene synthase, and are hence useful in treating diseases and medical conditions in which inhibition of squalene synthase is desirable.

According to the present invention there is provided a compound of formula I (formula set out hereinafter together with the other chemical formulae referred to herein), or a pharmaceutically acceptable salt thereof, wherein:

$R^1$ is hydrogen or hydroxy;

$R^2$ is hydrogen; or $R^1$ and $R^2$ are joined together so that $CR^1$–$CR^2$ is a double bond;

X is selected from —$CH_2CH_2$—, —CH=CH—, —C≡C—, —$CH_2O$—, —$CH_2NH$—, —$NHCH_2$—, —$CH_2CO$—, —$COCH_2$—, —$CH_2S$— and —$SCH_2$—;

$Ar^1$ is a phenylene moiety;

$Ar^2$ is a heteroaryl moiety;

and wherein one or both of $Ar^1$ and $Ar^2$ may optionally bear one or more substituents independently selected from halogeno, hydroxy, amino, nitro, cyano, carboxy, carbamoyl, (1–6C)alkyl, (2–6C)alkenyl, (2–6C)alkynyl, (1–6C)alkoxy, (1–6C)alkylamino, di-[(1–6C)alkyl]amino, N-(1–6C)alkylcarbamoyl, di-N,N-[(1–6C)alkyl]carbamoyl, (1–6C)alkoxycarbonyl, (1–6C)alkylthio, (1–6C)alkylsulphinyl, (1–6C)alkylsulphonyl, halogeno-(1–6C)alkyl, carboxy(1–6C)alkyl and (1–6C)alkanoylamino;

provided that when $R^1$ is hydroxy, X is not selected from —$NHCH_2$— and —$SCH_2$—.

It will be understood that when formula I compounds contain a chiral centre, the compounds of the invention may exist in, and be isolated in, optically active or racemic form. The invention includes any optically active or racemic form of a compound of formula I which possesses the beneficial pharmacological effect of inhibiting squalene synthase. The synthesis of optically active forms may be carried out by standard techniques of organic chemistry well known in the art, for example by, resolution of a racemic form, by synthesis from optically active starting materials or by asymmetric synthesis.

It will also be understood that, insofar as certain of the compounds of the formula I may exhibit the phenomenon of tautomerism, for example a compound of formula I in which $Ar^2$ bears a hydroxy substituent, the present invention includes any tautomeric form of a compound of formula I which possesses the beneficial pharmacological effect of inhibiting squalene synthase.

It is also to be understood that generic terms such as "alkyl" include both the straight chain and branched chain groups such as butyl and tert-butyl. However, when a specific term such as "butyl" is used, it is specific for the straight chain or "normal" butyl group, branched chain isomers such as "t-butyl" being referred to specifically when intended.

It will be appreciated that when $R^1$ and $R^2$ are joined so that $CR^1$–$CR^2$ is a double bond, the heterocyclic ring in formula I will comprise the 2,3-dehydroguinuclidine moiety shown in formula Ia.

As used herein, the term heteroaryl encompasses monocyclic aromatic heterocycles which contain (in addition to carbon atoms) one, two, three or four heteroatoms selected from nitrogen, oxygen and sulphur; bicyclic aromatic heterocycles of about 8 to 10 ring atoms and containing one, two, three or four heteroatoms selected from nitrogen, oxygen and sulphur, and in particular benz-derivatives of said monocyclic aromatic heterocycles.

Suitable values for $Ar^2$ include, for example, a 5-membered or 6-membered aromatic (that is, fully unsaturated) heterocyclic ring containing one, two, three or four heteroatoms (and in particular one, two or three heteroatoms) selected from nitrogen, oxygen and sulphur, and a 5-membered or 6-membered aromatic heterocyclic ring containing one, two, three or four heteroatoms (and in particular one, two or three heteroatoms) selected from nitrogen, oxygen and sulphur which is fused to a benzene ring.

In particular $Ar^2$ may comprise a heteroaryl moiety containing up to three heteroatoms selected from nitrogen, oxygen and sulphur. Thus, in particular, $Ar^2$ the heteroaryl moiety, may comprise a fully unsaturated heterocyclic ring which contains one, two or three heteroatoms selected from nitrogen, oxygen and sulphur as ring atoms, and may be attached to $Ar^1$ through any available ring atom.

Suitable values for $Ar^1$ the phenylene moiety, include 1,2-phenylene; 1,3-phenylene and 1,4-phenylene.

A particular value for an optional substituent which may be present on $Ar^1$ or $Ar^2$ is, for example, for alkyl; (1–4C)alkyl, such as methyl, ethyl, propyl, isopropyl, butyl, isobutyl or sec-butyl;

for alkenyl; (2–4C)alkenyl, such as allyl, prop-2-enyl, but-2-enyl or 2-methyl-2-propenyl;

for alkynyl; (2–4C)alkynyl, such as prop-2-ynyl or but-2-ynyl;

for alkoxy; (1–4C)alkoxy, such as methoxy, ethoxy, propoxy, isopropoxy or butoxy;

for alkylamino; (1–4C)alkylamino, such as methylamino, ethylamino, propylamino or butylamino;

for di-alkylamino; dimethylamino, diethylamino, methylpropylamino or dipropylamino;

for alkylcarbamoyl; N-methylcarbamoyl, N-ethylcarbamoyl or N-propylcarbamoyl;

for di-alkylcarbamoyl; N,N-dimethylcarbamoyl or N,N-diethylcarbamoyl;

for alkoxycarbonyl; methoxycarbonyl, ethoxycarbonyl or propoxycarbonyl;

for alkylthio; methylthio, ethylthio, propylthio, isopropylthio or butylthio;

for alkylsulphinyl; methylsulphinyl, ethylsulphinyl, propylsulphinyl, isopropylsulphinyl or butylsulphinyl;

for alkylsulphonyl; methylsulphonyl, ethylsulphonyl, propylsulphonyl, isoproylsulphonyl or butylsulphonyl;

for halogeno; fluoro, chloro, bromo or iodo;

for halogenoalkyl; halogenoalkyl containing one, two or three halo groups selected from fluoro, chloro, bromo and iodo and an alkyl group selected from methyl, ethyl, propyl, iso-propyl, butyl, iso-butyl and sec-butyl, (in particular fluoromethyl, difluoromethyl or trifluoromethyl);

for carboxyalkyl; carboxymethyl, 1-carboxyethyl, 2-carboxyethyl and 3-carboxypropyl; and for alkanoylamino; formamido, acetamido, propionamido, iso-propionamido, butyramido or iso-butyramido.

Particular values for $Ar^2$ include, for example, furyl, pyrrolyl, thienyl, pyridyl, pyrazinyl, pyrimidinyl, pyridazinyl, imidazolyl, oxazolyl, isooxazolyl, thiazolyl, isothiazolyl, oxadiazolyl, triazolyl, tetrazolyl, benzfuranyl, quinolyl, isoquinolyl, benzimidazolyl, indolyl, pyrazolyl, thiadiazolyl, benzthiazolyl and benzoxazolyl.

More particular values of $Ar^2$ include, for example, pyridyl, pyrazolyl, thiadiazolyl, benzthiadiazolyl and oxadiazolyl.

In general, it is preferred for example that $Ar^2$ is a 5-membered or 6-membered heteroaryl ring containing (in addition to carbon atoms) one, two or three heteroatoms selected from nitrogen, oxygen and sulphur. Thus preferred values for $Ar^2$ will include, for example, pyridyl, thiadiazolyl or oxadiazolyl (especially pyridyl or oxadiazolyl).

A particular value for $Ar^1$ is, for example, 1,3-phenylene or 1,4-phenylene.

In general it is preferred, for example, that $Ar^1$ is 1,4-phenylene.

In general, it is preferred that $Ar^1$ is optionally unsubstituted or substituted by one, two or three substituents independently selected from those mentioned above; and that $Ar^2$ is optionally unsubstituted or substituted by one, two or three substituents from those mentioned above.

In a particular embodiment, one or both of $Ar^1$ and $Ar^2$ may optionally bear one or more substituents selected from halogeno, hydroxy, nitro, (1–6C)alkyl, (2–6C)alkenyl, (1–6C)alkoxy, (1–6C)alkylthio, (1–6C)alkylsulphinyl, (1–6C)alkoxycarbonyl, (1–6C)alkylsulphonyl, (1–6C)alkanoylamino and halogeno-(1–6C)alkyl.

A particular value for X is, for example, —CH$_2$CH$_2$—, —CH=CH—, —C≡C—, —CH$_2$O—, —CH$_2$NH— or —CH$_2$S—. A more particular values for X is, for example, —CH$_2$CH$_2$—, —CH=CH—, —C≡C— or —CH$_2$O—. In general it is preferred, for example, that X is —CH=CH—, —C≡C— or —CH$_2$O—.

In general it is preferred, for example, that $R^1$ is hydroxy and $R^2$ is hydrogen.

Specific values of $Ar^2$ (optionally substituted as hereinbefore defined) include, for example, 2-pyridyl, 3-pyridyl, 4-pyridyl, 1-pyrrolyl, 5-pyrimidinyl, 2-indolyl, 2-quinolyl, 3-pyazolyl, 1-imidazolyl, 2-methyl-tetrazol-5-yl, 1-pyrazolyl, 2-oxazolyl, 5-isoxazolyl, 2-thiazolyl, 1,2,4-thiadiazol-5-yl, 2-benz-1,3-oxazolyl, 2-benz-1,3-thiazolyl, 1,2,4-oxadiazol-3-yl, 1,2,4-oxadiazol-5-yl and 1,3,4-oxadiazol-2-yl.

Specific optional substituents for $Ar^2$ include hydroxy, (1–6C)alkyl such as methyl, ethyl or isopropyl, (1–6C) alkoxy such as methoxy and (1–6C)alkoxycarbonyl such as ethoxycarbonyl.

Further specific values for $Ar^2$ include, for example, 2-thienyl, 2-pyridyl, 3-pyridyl, 4-pyridyl, 2-pyrimidyl, 5-pyrimidyl, 3-pyrazinyl, 2-pyridazinyl, 1-imidazolyl, 2-imidazolyl, 3-pyrazinyl, 2-pyridazinyl, 1,2,3-triazol-1-yl, 1,2,3-triazol-3-y, 3-quinolyl, 4-quinolyl, 3-isoquinolyl, 4-isoquinolyl, 1-benzimidazolyl, 2-indolyl and 3-indolyl, which may optionally bear one or two substituents independently selected from fluoro, chloro, bromo, iodo, hydroxy, nitro, methyl, ethyl, propyl, isopropyl, butyl, isobutyl, sec-butyl, allyl, methoxy, ethoxy, propoxy, isopropoxy, butoxy, methylthio, ethylthio, propylthio, isopropylthio, butylthio, methylsulphinyl, ethylsulphinyl, propylsulphinyl, isopropylsulphinyl, butylsulphinyl, methylsulphonyl, ethylsulphonyl, propylsulphonyl, isoproylsulphonyl, butylsulphonyl, acetamido, propionamido, iso-propionamido, fluoromethyl, difluoromethyl and trifluoromethyl.

Specific values for $Ar^1$ include, for example, an unsubstituted 1,4-phenylene moiety and a 1,4-phenylene moiety having one or substituents independently selected from fluoro, chloro, bromo, iodo, hydroxy, nitro, methyl, ethyl, propyl, isopropyl, butyl, isobutyl, sec-butyl, allyl, methoxy, ethoxy, propoxy, isopropoxy, butoxy, methylthio, ethylthio, propylthio, isopropylthio, butylthio, methylsulphinyl, ethylsulphinyl, propylsulphinyl, isopropylsulphinyl, butylsulphinyl, methylsulphonyl, ethylsulphonyl, propylsulphonyl, isoproylsulphonyl, butylsulphonyl, acetamido, propionamido, iso-propionamido, fluoromethyl, difluoromethyl and trifluoromethyl.

A preferred optional substituent for $Ar^1$ is for example, (2–6C)alkenyl such as allyl.

In a specific embodiment $Ar^1$ and $Ar^2$ are both unsubstituted.

In a further embodiment of the present invention, $R^1$ and $R^2$ are both hydrogen; and $Ar^1$ and $Ar^2$ have any of the meanings defined above.

In a further embodiment of the present invention, $R^1$ is hydroxy; $R^2$ is hydrogen; and $Ar^1$ and $Ar^2$ have any of the meanings defined above.

In a further embodiment of the present invention, $R^1$ and $R^2$ are joined together so that $CR^1$–$CR^2$ is a double bond; and $Ar^1$ and $Ar^2$ have any of the meanings defined above.

In a further embodiment of the present invention there is provided a compound of formula I, or a pharmaceutically acceptable salt thereof, wherein:

$R^1$ is hydrogen or hydroxy;

$R^2$ is hydrogen; or $R^1$ and $R^2$ are joined together so that $CR^1$–$CR^2$ is a double bond;

X is selected from —$CH_2CH_2$—, —CH=CH—, —C≡C—, —$CH_2O$—, —$OCH_2$—, —$CH_2NH$—, —$NHCH_2$—, —$CH_2CO$—, —$COCH_2$—, —$CH_2S$— and —$SCH_2$—;

$Ar^1$ is a phenylene moiety;

$Ar^2$ is a heteroaryl moiety containing up to three heteroatoms selected from nitrogen, oxygen and sulphur;

and wherein one or both of $Ar^1$ and $Ar^2$ may optionally bear one or more substituents independently selected from halogeno, hydroxy, amino, nitro, cyano, carboxy, carbamoyl, (1–6C)alkyl, (2–6C)alkenyl, (2–6C)alkynyl, (1–6C)alkoxy, (1–6C)alkylamino, di-[(1–6C)alkyl]amino, N-(1–6C)alkylcarbamoyl, di-N,N-[(1–6C)alkyl]carbamoyl, (1–6C)alkoxycarbonyl, (1–6C)alkylthio, (1–6C)alkylsulphinyl, (1–6C)alkylsulphonyl, halogeno-(1–6C)alkyl, carboxy(1–6C)alkyl and (1–6C)alkanoylamino;

provided that when $R^1$ is hydroxy, X is not selected from —$NHCH_2$— and —$SCH_2$—;

and excluding those compounds in which X is —$OCH_2$— and $R^1$ and $R^2$ are both hydrogen or $R^1$ and $R^2$ are joined together so that $CR^1$–$CR^2$ is a double bond, and their pharmaceutically acceptable salts.

Particular, preferred and specific values are the appropriate values mentioned above. Thus it is generally preferred that $R^1$ is hydroxy and $R^2$ is hydrogen.

In a particular, one or both of $Ar^1$ and $Ar^2$ may optionally bear one or more substituents selected from halogeno, hydroxy, nitro, (1–6C)alkyl, (2–6C)alkenyl, (1–6C)alkoxy, (1–6C)alkylthio, (1–6C)alkylsulphinyl, (1–6C)alkylsulphonyl, (1–6C)alkanoylamino and halogeno-(1–6C)alkyl.

In particular, $Ar^2$ is, for example, furyl, pyrrolyl, thienyl, pyridyl, pyrazinyl, primidinyl, pyridazinyl, imidazolyl, oxazolyl, isooxazolyl, thiazolyl, isothiazolyl, oxadiazolyl, thiazolyl, 1,2,3-triazolyl, 1,2,4-triazolyl, benzfuranyl, quinolyl, isoquinolyl, benzimidazolyl and indolyl.

A further group of values for $Ar^2$ of interest is, for example, pyridyl, pyrazinyl, primidinyl, pyridazinyl and imidazolyl (especially pyridyl such as 2-pyridyl or 3-pyridyl and imidazolyl such as 1-imidazolyl).

Values of interest for $Ar^2$ include pyridyl; values of interest for X include —CH=CH— or —C≡C—.

In a particular embodiment the present invention provides a compound of formula I, or a pharmaceutically acceptable salt thereof, wherein:

$R^1$ is hydrogen or hydroxy; $R^2$ is hydrogen; or $R^1$ and $R^2$ are joined together so that $CR^1$–$CR^2$ is a double bond;

X is selected from —$CH_2CH_2$—, —CH=CH—, —C≡C—, —$CH_2O$—, —$CH_2NH$—, and —$CH_2S$—;

$Ar^1$ is a 1,4-phenylene moiety;

$Ar^2$ is a heteroaryl moiety containing one, two or three heteroatoms selected from nitrogen, oxygen and sulphur;

and wherein one or both of $Ar^1$ and $Ar^2$ may optionally bear one or more substituents independently selected from halogeno, hydroxy, amino, nitro, cyano, carboxy, carbamoyl, (1–6C)alkyl, (2–6C)alkenyl, (2–6C)alkynyl, (1–6C)alkoxy, (1–6C)alkylamino, di-[(1–6C)alkyl]amino, N-(1–6C)alkylcarbamoyl, di-N,N-[(1–6C)alkyl]carbamoyl, (1–6C)alkoxycarbonyl, (1–6C)alkylthio, (1–6C)alkylsulphinyl, (1–6C)alkylsulphonyl, halogeno (1–6C)alkyl, carboxy(1–6C)alkyl and (1–6C)alkanoylamino.

Particular, preferred and specific values are the appropriate values mentioned above.

In a further embodiment of interest there is provided a compound of formula I, or a pharmaceutically acceptable salt thereof, wherein:

$R^1$ is hydroxy; $R^2$ is hydrogen; X is selected from —$CH_2CH_2$—, —CH=CH—, —C≡C— and —$CH_2O$—;

$Ar^1$ is a 1,4-phenylene moiety;

$Ar^2$ is a 5-membered or 6-membered heteroaryl moiety containing one or two nitrogen atoms (especially pyridyl or imidazolyl);

and wherein one or both of $Ar^1$ and $Ar^2$ may optionally bear one or more substituents independently selected from halogeno, hydroxy, amino, nitro, cyano, carboxy, carbamoyl, (1–6C)alkyl, (2–6C)alkenyl, (2–6c)alkynyl, (1–6C)alkoxy, (1–6C)alkylamino, di-[(1–6C)alkyl]amino, N-(1–6C)alkylcarbamoyl, di-N,N-[(1–6C)alkyl]carbamoyl, (1–6C)alkoxycarbonyl, (1–6C)alkylthio, (1–6C)alkylsulphinyl, (1–6C)alkylsulphonyl, halogeno (1–6C)alkyl, carboxy(1–6C)alkyl and (1–6C)alkanoylamino.

Particular, preferred and specific values are the appropriate values mentioned above.

In a particular embodiment the present invention provides a compound of formula I, or a pharmaceutically acceptable salt thereof, wherein:

$R^1$ is hydroxy; $R^2$ is hydrogen;

X is selected from —CH=CH—, —C≡C— and —$CH_2O$—;

$Ar^1$ is a 1,4-phenylene moiety;

$Ar^2$ is a heteroaryl moiety containing one, two or three heteroatoms selected from nitrogen, oxygen and sulphur;

and wherein one or both of $Ar^1$ and $Ar^2$ may optionally bear one or more substituents independently selected from halogeno, hydroxy, amino, nitro, cyano, carboxy, carbamoyl, (1–6C)alkyl, (2–6C)alkenyl, (2–6C)alkynyl, (1–6C)alkoxy, (1–6C)alkylamino, di-[(1–6C)alkyl]amino, N-(1–6C)alkylcarbamoyl, di-N,N-[(1–6C)alkyl]carbamoyl, (1–6C)alkoxycarbonyl, (1–6C)alkylthio, (1–6C)alkylsulphinyl, (1–6C)alkylsulphonyl, halogeno(1–6C)alkyl, carboxy(1–6C)alkyl and (1–6C)alkanoylamino.

Particular, preferred and specific values are the appropriate values mentioned above.

In a further embodiment the present invention provides a compound of formula I, or a pharmaceutically acceptable salt thereof, wherein:

$R^1$ is hydroxy; $R^2$ is hydrogen; X is selected from $-CH_2CH_2-$, $-CH=CH-$, $-C{\equiv}C-$ and $-CH_2O-$; $Ar^1$ is a 1,4-phenylene moiety; and $Ar^2$ is a 5- or 6-memebered heteroaryl moiety containing up to three heteroatoms independently selected from nitrogen, oxygen and sulphur;

and wherein one or both of $Ar^1$ and $Ar^2$ may optionally bear one or more substituents independently selected from halogeno, hydroxy, amino, nitro, cyano, carboxy, carbamoyl, (1–6C)alkyl, (2–6C)alkenyl, (2–6C)alkynyl, (1–6C)alkoxy, (1–6C)alkylamino, di-[(1–6C)alkyl]amino, N-(1–6C)alkylcarbamoyl, di-N,N-[(1–6C)alkyl]carbamoyl, (1–6C)alkoxycarbonyl, (1–6C)alkylthio, (1–6C)alkylsulphinyl, (1–6C)alkylsulphonyl, halogeno-(1–6C)alkyl, carboxy(1–6C)alkyl and (1–6C)alkanoylamino.

Particular, preferred and specific values are the appropriate values mentioned above.

Further compounds (and their pharmaceutcially acceptable salts of interest include, for example those in which:

(a) $R^1$ is hydroxyl $R^2$ is hydrogen; X is $-C{\equiv}C-$; $Ar^1$ is a 1,4-phenylene moiety; and $Ar^2$ is a 5- or 6-memebered heteroaryl moiety containing up to three heteroatoms independently selected from nitrogen, oxygen and sulphur (especially oxadiazolyl or thiadiazolyl);

(b) $R^1$ is hydroxy; $R^2$ is hydrogen; X is selected from $-CH_2CH_2-$, $-CH=CH-$, $-C{\equiv}C-$ and $-CH_2O-$; $Ar^1$ is a 1,4-phenylene moiety; and $Ar^2$ is an oxadiazolyl moiety;

(c) $R^1$ is hydroxy; $R^2$ is hydrogen; X is $-CH_2O-$; $Ar^1$ is a 1,4-phenylene moiety; and $Ar^2$ is a 5- or 6-memebered heteroaryl moiety containing up to three heteroatoms independently selected from nitrogen, oxygen and sulphur (especially oxadiazolyl or thiadiazolyl); and in each case one or both of $Ar^1$ and $Ar^2$ may optionally bear one or more substituents independently selected from halogeno, hydroxy, amino, nitro; cyano, carboxy, carbamoyl, (1–6C)alkyl, (2–6C)alkenyl, (2–6C)alkynyl, (1–6C)alkoxy, (1–6C) alkylamino, di-[(1–6C)alkyl]amino, N-(1–6C) alkylcarbamoyl, di-N,N-[(1–6C)alkyl]carbamoyl, (1–6C)alkoxycarbonyl, (1–6C)alkylthio, (1–6C) alkylsulphinyl, (1–6C)alkylsulphonyl, halogeno-(1–6C)alkyl, carboxy(1–6C)alkyl and (1–6C)alkanoylamino.

Further compounds (and pharmaceutically acceptable salts thereof) of interest include those of formula I wherein:

$R^1$ is hydroxy; $R^2$ is hydrogen; X is selected from $-CH_2CH_2-$, $-CH=CH-$, $-C{\equiv}C$ and $-CH_2O-$ (especially $-CH=CH-$ or $-C{\equiv}C$);

$Ar^1$ is a 1,4-phenylene moiety; and $Ar^2$ is a pyridyl moiety.

Compounds of the invention which are of particular interest include the compounds described in the accompanying Examples (and their pharmaceutically-acceptable salts), and are hence provided as a further feature of the present invention. In particular the present invention provides a compound (or a pharmaceutically acceptable salt) selected from those described in Examples 4, 8, 11, 31, 32, 33, 34, 41, 43, 44 and 49.

A suitable pharmaceutically-acceptable salt of the present invention comprises an acid-addition salt derived from an inorganic or organic acid which provides a pharmaceutically-acceptable anion. Thus, examples of salts of the present invention include acid-addition salts with hydrochloric, hydrobromic, nitric, sulphuric, phosphoric, trifluoroacetic, citric, tartaric, succinic, maleic, fumaric or acetic acid. In addition, suitable pharmaceutically-acceptable salts include [where the compound of formula I is sufficiently acidic, for example where the compound of formula I bears an acidic substituent such as carboxy] those formed with a base which affords a pharmaceutically acceptable cation. Suitable bases include an alkali metal salt (such as a sodium or potassium salt), an alkaline earth metal salt (such as a calcium or magnesium salt), an ammonium salt or a salt with an organic base which affords a physiologically-acceptable cation such as a salt with methylamine, dimethylamine, triethylamine, piperidine or morpholine.

The compounds of the present invention may be obtained by standard procedures of organic chemistry already known to be applicable to the preparation of structurally analogous compounds. Such procedures for the preparation of the compounds of formula I, or pharmaceutically acceptable salts thereof, are provided as a further feature of the present invention and are illustrated by the following processes in which the various generic radicals, for example, $R^1$, $R^2$, X, $Ar^1$ and $Ar^2$ may take any of the meanings hereinbefore defined.

Thus, according to the present invention there is also provided a process for preparing a compound of formula I, or a pharmaceutically-acceptable salt thereof, which process comprises:

(a) For those compounds of formula I in which $R^1$ and $R^2$ are both hydrogen, reducing a compound of formula I in which $R^1$ and $R^2$ are joined together so that $CR^1-CR^2$ is a double bond.

The reduction may be carried out, for example, by catalytic hydrogenation, or by reaction with a suitable reducing agent. Suitable reaction conditions include, for example, catalytic hydrogenation using a catalyst which comprises a noble metal. Particular catalysts include palladium, platinum and nickel (especially when in the finely divided state known as raney nickel), and catalysts in which the noble metal is supported on an inert carrier such as carbon. A specific example of a supported catalyst is Pd/C. The reduction is conveniently carried out in a solvent of, for example, an alcohol (such as ethanol), and at (or near) ambient temperature and optionally under pressure.

Further suitable reaction conditions include, for example, reduction with a borane such as diborane. The reaction is generally carried out in an inert solvent of, for example, tetrahydrofuran or methyl t-butyl ether at, for example, 0°–60° C. It may be preferable to cool the reaction below ambient temperature (e.g. to about 0° C.) during the reduction. The borane generated may be hydrolysed by treatment with an organic acid such as acetic acid, which hydrolysis may be carried out at 0°–60° C., and may be accelerated by heating (e.g. refluxing).

(b) For compounds of formula I in which $R^1$ and $R^2$ are joined together so that $CR^1-CR^2$ is a double bond, dehydrating a compound of formula I in which $R^1$ is hydroxy and $R^2$ is hydrogen.

The dehydration may be carried out using an acid such as sulphuric acid (e.g. concentrated sulphuric acid), or p-toluene sulphonic acid. The reaction is conveniently carried out with heating, and conveniently an inert solvent is employed. For example, the reaction may be carried out using sulphuric acid at temperatures of about 70°–130° C.; or using p-toluene sulphonic acid in a hydrocarbon solvent of, for example, toluene or xylene at ambient temperature to reflux, and preferably at reflux. The dehydration may also be carried out using trifluoroacetic acid in an inert solvent such as dichloromethane (at ambient temperature to reflux temperature).

(c) For compounds of formula I in which $R^1$ and $R^2$ are joined together so that $CR^1$-$CR^2$ is a double bond, treating a compound of formula II in which Z is a leaving group with a base.

Suitable values for Z include, for example, halogen such as chloro, bromo, iodo, or a methylsulphonyloxy or toluenesulphonyloxy group. Suitable bases include hydroxide (such as potassium or sodium hydroxide), and alkoxide (such as potassium t-butoxide or sodium ethoxide).

The reaction is conveniently carried out in the presence of a solvent, preferably a polar organic solvent. Suitable solvents include, for example, an alcohol (such as ethanol), or an aprotic solvent such as dimethylformamide or N-methylpyrrolidone. The reaction may be carried out at ambient temperature or at an elevated temperature, such as at a temperature between ambient and the reflux temperature of the reaction mixture. This method is generally preferred over that described in (b) when X is —$OCH_2$— or —$SCH_2$—.

The compounds of formula II may be prepared from a compound of formula I in which $R^1$ is hydroxy. For example, where Z is halogen the compound of formula I in which $R^1$ is hydroxy and $R^2$ is hydrogen may be reacted with the appropriate phosphorous halide (e.g. $PCl_5$, $PBr_3$ or $PI_3$), or where Z is chloro, by reaction with thionyl chloride. The compound of formula I in which $R^1$ is hydroxy may be reacted with mesyl chloride to the compound in which Z is methylsulphonyloxy; and with tosyl chloride to give Z is toluene sulphonyloxy.

(d) For those compounds of formula I in which X is —$CH_2CO$—, reacting an organometallic compound of formula $Ar^2$—$Ar^1$—M in which M is a metal atom or a derivative thereof, with a compound of formula III.

Suitable values for M include, for example, magnesium and lithium. In the case where M is magnesium it is conveniently present in the form of a derivative of formula —MgX where X is a halogen atom such as iodo or bromo, so that the organometallic compound of formula III is in the form known as a Grignard Reagent. The reaction is generally carried out in an inert solvent such as dry diethyl ether or tetrahydrofuran. For example, the reaction may be carried out at a temperature between 0° C. and the reflux temperature of the reaction mixture.

The compounds of formula $Ar^2$—$Ar^1$—M may be prepared from the corresponding compound of formula $Ar^2$—$Ar^1$-"hal" in which "hal" is a halogen atom, such as iodo or bromo as is yell known in the art.

e) For those compounds of formula I in which X is —$CH_2$—NH— or —$NHCH_2$—, reducing a compound of formula I in which X is —CH=N— or —N=CH— (as appropriate).

The reaction may be carried out using a chemical reducing agent such as a hydride in a solvent such as an alcohol at ambient temperature. Thus, in a particular example, the reduction may be carried out using sodium borohydride in a solvent of methanol at ambient temperature. The reduction may also be carried out by selective catalytic hydrogenation using similar conditions to those described under (a) above.

It will be appreciated that the preferred method of reduction will depend upon the value of X. Thus, for example, where debenzylation is possible (e.g. when X is —$NHCH_2$—), it is generally preferred that a chemical reducing agent is employed.

The compounds of formula I in which X is —CH=N— may be prepared by reaction of a compound of formula IV with a compound of formula $Ar^2$—$Ar^1$—$NH_2$. The reaction is generally carried out in an inert hydrocarbon solvent such as toluene or benzene, with heating (e.g. at reflux) and the reaction may be accelerated by removing water generated in the reaction by azeotropic distillation. Similarly, the compounds of formula I in which X is —N=CH— may be prepared by reaction of a compound of formula $Ar^2$—$Ar^1$—CHO with a compound of formula V.

f) For those compounds of formula I in which X is —$CH_2NH$—, —$CH_2O$—, —$CH_2S$—, $R^1$ is hydroxy and $R^2$ is hydrogen, reacting a compound of formula $Ar^2$—$Ar^1$—Z in which Z is —$NH_2$, —OH or SH as appropriate with a compound of formula VI.

The reaction is conveniently carried out in a solvent such an inert hydrocarbon e.g. toluene with heating. The reaction may be facilitated by the presence of acid or base.

The compound of formula VI is conveniently generated in situ, by, for example, treating quinuclidin-3-one with trimethylsulphoxonium iodide in the presence of a base of, for example, an alkali metal hydride such as sodium hydride and in a solvent such as dimethylformamide, or an alkali metal hydroxide such as sodium hydroxide in a solvent such as an aqueous solvent.

The compound of formula VI may also be prepared from a "halohydrin" as is well known in the art. The halohydrin may be prepared, for example, by addition of HOCl to the corresponding olefin and the halohydrin treated with base (e.g. NaOH) to give the compound of formula VI.

g) For compounds of formula I in which X is —CH=CH—, reacting a compound of formula VII with a compound of formula IV in the presence of a base.

Suitable bases include alkoxides, such as potassium t-butoxide, and the reaction is conveniently carried out in an inert solvent such as tetrahydrofuran with cooling below ambient temperature e.g. -40° C. to 0° C.); and metal hydrides such as sodium hydride in a solvent such as dimethyl formamide or dimethylsuphoxide. A particularly suitable base is, for example, sodium dimsyl which may conveniently be used in a solvent such as dimethyl suphoxide.

The compounds of formula XI may be prepared by reaction of a compound of formula $Ar^2$—$Ar^1$—$CH_2$-hal in which "hal" is halogen, such as chloro, with triphenylphosphine as is well known in the art.

h) For those compounds of formula I in which X is —$CH_2CH_2$—, reducing a compound of formula I in which X is —CH=CH—.

The reaction may conveniently be carried out by catalytic hydrogenation using conditions similar to those mentioned in (a) above.

In an alternative synthesis a compound of formula $Ar^2$—$Ar^1$—$CH_2CH_2$-hal wherein "hal" represents a halogen atom such as bromo, is reacted with quinuclidin-3-one in the presence of sec-butyl lithium, with cooling (e.g. -70° C.) in an inert solvent such as tetrahydrofuran.

i) For compounds of formula I in which X is —$COCH_2$—, reacting a compound of formula $Ar^2$—$Ar^1$—$CH_2$—M in which M is a metal atom or a derivative thereof, with a compound of formula VIII.

Suitable values for M and suitable reaction conditions are those mentioned in (d) above. The compounds of formula $Ar^2$—$Ar^1$—$CH_2$—M may be prepared from the corresponding halogeno compound in a manner analogous to the preparation of compounds of formula $Ar^2$—$Ar^1$—M discussed in (d) above.

j) For those compounds of formula I in which X is —CH$_2$O— or —CH$_2$S— and R$^1$ and R$^2$ are hydrogen, reacting a compound of formula Ar$^2$—Ar$^1$—CH$_2$—Z$^1$ with a compound of formula IX, in which Z$^1$ is a leaving group and Z$^2$ is —YM, or Z$^1$ is —YM and Z$^2$ is a leaving group, and wherein Y is oxygen or sulphur (as appropriate) and M is a metal atom.

Suitable leaving groups include, for example, halogen (such as chloro, bromo or iodo), methanesulphonyloxy, toluenesulphonyloxy or trifluoromethanesulphonyloxy; and suitable metals include, for example sodium and lithium.

The process is generally performed in the presence of a suitable solvent, for example, a hydrocarbon, such as toluene or xylene, or an ether such as dioxan or tetrahydrofuran, and at a temperature in the range, for example 20°–150° C.

It may be desirable to protect the quinuclidine nitrogen atom during the reaction, especially when Z$^1$ is —YM, as described in (l) below. It may be desirable to protect R$^1$ when it represents a hydroxy group as, for example, a silyl ether.

k) For those compounds of formula I in which X is —CH$_2$O— or —CH$_2$S— and R$^1$ and R$^2$ are both hydrogen, reacting a compound of formula Ar$^2$—Ar$^1$—YH in which Y is oxygen or sulphur as appropriate with a compound of formula X in which Z is a leaving group.

Suitable leaving groups include halogen, such as chloro, bromo or iodo, methanesulphonyloxy and toluenesulphonyloxy. The reaction is generally carried out in the presence of a base such as an alkali metal hydroxide, e.g. sodium or potassium hydroxide, and in a solvent such as dimethylsulphoxide or dimethylformamide.

l) For compounds of formula I in which X is —OCH$_2$—, —SCH$_2$—, —CH2O—, or —CH$_2$S—, deprotecting a compound of formula XI in which Q is a protecting group, R1 is hydrogen or hydroxy and R2 is hydrogen.

Suitable values for Q include, for example, —BH$_3$ or an oxygen atom. When Q is —BH$_3$ the deprotection may be carried out by treatment with an acid such as hydrochloric acid in a solvent such as acetone. When Q is an oxygen atom deprotection may be carried out by reduction using a suitable reducing agent such as sulphur dioxide.

The compounds of formula XI in which X is —CH$_2$O— or —CH$_2$S— may be prepared by methods analogous to those described in (j), and in which X is —OCH$_2$— or —SCH$_2$— by methods analogous to those described in (k) above, but in which the starting material containing the quinuclidine moiety is protected by Q. A preferred way of preparing compounds of formula XI in which X is —CH$_2$O— or —CH$_2$S— and R$^1$ is hydroxy and R$^2$ is hydrogen is by a procedure analogous to that described in (f) in which the compound of formula VI is protected by Q. The quinuclidine moiety in the various starting materials may be protected using methodology well known in the art. Thus, for example, those in which Q is BH$_3$ may be prepared by reaction of the appropriate quinuclidine moiety with BH$_3$.THF, generally with cooling (for example at –70° C.); whilst those in which Q is an oxygen atom may be prepared by oxidation of the appropriate quinuclidine moiety with, for example, 30% hydrogen peroxide.

m) For those compounds of formula I in which X is —C≡C—, reacting a compound of formula I in which X is —CH=CH— with a halogen, followed by treatment with a base.

A suitable halogen is bromine and the reaction is conveniently carried out in an inert solvent such as carbon tetrachloride. Suitable bases include, for example, potassium t-butoxide. This treatment is conveniently carried out in a solvent such as THF, with heating (e.g. at a temperature between ambient and about 70° C.).

n) For those compounds of formula I in which R$^1$ is hydroxy, R$^2$ is hydrogen and X is —C≡C—, reacting a compound of formula Ar$^2$—Ar$^1$—C≡C—M in which M is a metal atom, with quinuclidin-3-one.

A suitable metal is lithium and suitable reaction conditions include those mentioned in (d) above.

o) For those compounds in which R$^1$ and R$^2$ are hydrogen and X is —C≡C—, reacting a compound of formula Ar$^2$—Ar$^1$—C≡C—M in which M is a metal atom with a compound of formula IX in which Z is a leaving group and R$^1$ and R$^2$ are hydrogen.

Suitable values for Z include, for example, halogen (such as chloro, bromo or iodo), methanesulphonyloxy, toluenesulphonyloxy or trifluoromethanesulphonyloxy; suitable values for M include, for example, lithium; and suitable reaction conditions include those mentioned under (d) above.

p) For those compounds in which X is —C≡C— and R$^1$ is hydrogen or hydroxy and R$^2$ is hydrogen, reacting a compound of formula XII in which R$^1$ is hydrogen or hydroxy and R$^2$ is hydrogen with a compound of formula Ar$^2$—Ar$^1$—Z in which Z is a leaving group in the presence of a catalyst.

Suitable catalysts include, for example, transition metal complexes such as palladium or nickel complexes. Particular catalysts are palladium (II) complexes, a specific example of which is Pd(PPh$_3$)$_2$Cl$_2$. Suitable values for Z include, for example, halogen (such as chloro, bromo or iodo), methanesulphonyloxy, toluenesulphonyloxy and trifluoromethanesulphonyloxy. The reaction is generally carried out in the presence of a base, for example, an amine such as triethylamine and in a solvent such as dimethylformamide with heating (for example at 60° to 100° C.). The reaction is preferably carried out in the prersence of copper (I)iodide. Compounds of formula XII may be prepared according to Scheme 1a and 2b.

q) For those compounds in which X is —C=C— and R$^1$ is hydrogen or hydroxy and R$^2$ is hydrogen, reacting a compound of formula XIII in which R$^1$ is hydrogen or hydroxy and R$^2$ is hydrogen with a compound of formula Ar$^2$—Ar$^1$—Z in which Z is a leaving group in the presence of a catalyst.

Suitable reaction conditions are those mentioned under (p) above. Compounds of formula XIII may be prepared according to Scheme 1b and 2a.

r) For those compounds of formula I in which R$^1$ is hydrogen or hydroxy and R$^2$ is hydrogen, reacting a compound of formula Ar$^2$M wherein M is a metal atom or a metal atom having suitable ligands with a compound of formula XIV wherein Z is a leaving group, in the presence of a catalyst.

Suitable values for Z include, for example, halogen such as bromo or iodo, and a trifluoromethanesulphonyloxy group. Suitable values for the metal atom include, for example, copper and lithium. Suitable values for a metal atom having suitable ligands include, for example, those which contain a tin, boron, silicon, zirconium, aluminium, magnesium or mercury atom. Suitable ligands include, for example, alkyl groups (such as methyl, ethyl, propyl or butyl); halogen (such as fluoro, bromo or iodo); and hydroxy. Particular ligands include, for example, for tin, three substituents independently selected from (1–6C)alkyl (such as methyl, ethyl, propyl or butyl); for silicon a substituent selected from methyl and fluoro together with two fluoro atoms; for zirconium atom a halogeno group (such as fluoro, chloro, bromo or iodo) and two cyclopentadienyl radicals; for aluminium, two groups independently selected from (1–6C)alkyl (such as methyl, ethyl, propyl or butyl); for mercury atom a single group selected from a halogeno (such as fluoro, chloro, bromo or iodo), trifluoroacetyloxy or acetyloxy group; for magnesium, a halogeno group (such as fluoro, chloro, bromo or iodo); and for boron two groups independently selected from hydroxy, (1–4C) alkoxy (such as methoxy or ethoxy) and (1–6C)alkyl (such as methyl, ethyl, propyl or butyl). In the case of boron, the groups may, together with the boron atom to which they are attached, form a boroxin ring.

A particularly suitable value for a metal atom having suitable ligands is the group —B(OH)$_2$.

Suitable catalysts include, for example, a catalyst selected from a palladium (0), palladium (II), nickel (0) and nickel (II) catalyst. Particular catalysts include, for example, tetrakis-(triphenylphosphine)nickel(0), bis(triphenylphosphine)nickel(II) chloride, nickel(II)chloride, palladium(II)chloride, bis(triphenylphosphine)palladium(II) chloride, bis(triphenylphosphine)phenylpalladium iodide and tetrakis(triphenylphosphine)palladium(0). A radical initiator, for example, azo(bisisobutyronitrile) may also be present.

The process is generally performed in the presence of a suitable solvent or diluent, for example, a hydrocarbon, such as toluene or xylene, or an ether such as dioxan or tetrahydrofuran, and at a temperature in the range, for example, 20°–150° C.

Compounds of the formula Ar$^2$M are known or may be obtained by analogy therewith or, for example, by reaction of a compound of the formula M.Hal wherein M is the metal atom (defined above) and Hal is a halogeno group such as chloro, bromo or iodo, with a Grignard reagent or aryllithium compound derived, using standard procedures, from a compound of the formula Ar$^2$-hal wherein hal is a halogeno group such as chloro, bromo or iodo. The reaction is generally carried out in a solvent such as tetrahydrofuran or ether, or a mixture thereof, and at a temperature of –78° C. to 25° C. In the case where the group which comprises a boron atom having ligands selected from alkoxy and hydroxy, the compounds of formula Ar$^2$M may also be prepared by reaction of a trialkylboronate of the formula B(OR)$_3$ wherein R is a (1–6C)alkyl group with a Grignard reagent or aryllithium compound derived, using standard procedures, from a compound of the formula Ar$^2$-hal wherein hal is a halogeno group such as chloro, bromo or iodo. The reaction is generally carried out in a solvent such as tetrahydrofuran or ether, or a mixture thereof, and at a temperature of –78° C. to 25° C. The compounds of formula Ar$^2$M wherein the ligands attached to boron are alkoxy can be converted to those in which the ligands are hydoxy using standard techniques. The boroxin derivatives may be prepared from the latter compounds by dehydration using standard procedures.

Compounds of formula XIV may be prepared using analogous methods to those described above for the preparation of compounds of formula I.

s) For those compounds of formula I in which R$^1$ is hydrogen or hydroxy and R$^2$ is hydrogen, reacting a compound of formula XV wherein M is a metal atom or a metal atom having suitable ligands with a compound of formula Ar$^2$Z wherein Z is a leaving group, in the presence of a catalyst.

Suitable values for M and Z and reaction conditions are those mentioned above (r).

Compounds of formula Ar$^2$Z are readily available or may be prepared by methods well known in the art. Compounds of formula XV may be readily prepared by methods well known in the art, for example by from compounds of formula XIV in an analogous manner to the preparation of compounds of formula Ar$^2$M described above.

The various starting materials referred to in (a) to (s) above are readily available or may be prepared by methods well known on the art. For example, starting materials having the bi-aryl ring system Ar$^2$—Ar$^1$ may be prepared by coupling the appropriately substituted rings Ar$^2$ and Ar$^1$ using a procedure analogous to that described in (r) and (s) above. Thus, for example, Ar$^2$—Ar$^1$-hal used in (d) above may be prepared by reaction of a compound of formula Ar$^2$—M (wherein M is a metal or a metal having suitable ligands) with a compound of formula Z—Ar$^1$-"hal" (wherein Z is a leaving group) in the presence of a catalyst as described in (r) below, or by the reaction of a compound of formula M—Ar$^1$-hal with a compound of formula Ar$^2$—Z as described in (s) below.

t) For those compounds of formula I in which X is —CH=CH—, reacting a compound of formula XVI in which L is a suitable ligand with a compound of formula Ar$^2$—Ar$^1$—Z in which Z is a leaving group in the presence of a catalyst.

Suitable values for L include, for example, (1–6C)alkyl with butyl being preferred. Suitable values for Z, suitable catalysts and reaction conditions include those mentioned under (r) above. A particularly suitable catalyst is, for example, tris(dibenzylideneacetone)palladium [0].

It will be appreciated that in some of the reactions mentioned herein it may be necessary/desirable to protect any sensitive groups in the compounds. The instances where protection is necessary or desirable and suitable methods for protection are known to those skilled in the art. Thus, if reactants include groups such as amino, carboxy or hydroxy it may be desirable to protect the group in some of the reactions mentioned herein. Suitable protecting groups for hydroxy include, for example, silyl groups such as trimethylsilyl or t-butyldimethylsilyl, tetrahydropyranyl and esterifing groups such as a methyl or ethyl ester; and for amino groups include benzyloxycarbonyl and t-butoxycarbonyl. Carboxy groups may be protected in a reduced form such as in the form of the corresponding protected alcohol, which may be subsequently oxidised to give the carboxy group. The protecting groups may be removed at any convenient stage in the synthesis using conventional techniques well known in the chemical art.

It will also be appreciated that the preferred process for preparing a particular compound of formula I will depend upon the nature of the various radicals. Similarly, the preferred choice of reagent will depend upon the nature of the various radicals present. For example, when it is required to reduce a particular compound the reducing agent will generally be selected to be one which does not interfere with other groupings present.

It will also be appreciated that certain of the various optional substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acylhalide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

It will be appreciated that when a pharmaceutically acceptable salt is required it may be prepared by reacting the compound of formula I with an acid which affords a physiologically acceptable anion or a base which affords a physiologically acceptable cation, or by any other conventional salt formation process.

As mentioned previously, the compounds of the formula I (and their pharmaceutically-acceptable salts) are inhibitors of the enzyme squalene synthase. Thus the compounds of the present invention are capable of inhibiting cholesterol biosynthesis by inhibition of de novo squalene production.

The beneficial pharmacological properties of the compounds of the present invention may be demonstrated using one or more of the following techniques.

(a) Inhibition of Squalene synthase

In this test, the ability of a compound to prevent the formation of squalene from a radioactive substrate (tritiated farnesyl pyrophosphate) is assessed.

The test compound is incubated at a concentration of 25 micromolar in 200 μl of a buffered solution containing potassium phosphate (50 mM), $MgCl_2$ (4.95 mM), KF (9.9 mM), NADPH (0.9 mM) and rat liver microsomal protein (20 μg). Rat liver microsomes are prepared by the method described in published European Patent Application No. 324,421 and stored in liquid nitrogen prior to assay. Assay vials are kept at 37° C. throughout the incubation.

The reaction is started with the addition of the substrate (1-[$^3$H]-farnesyl pyrophosphate), final concentration 20 μM, and stopped after 15 minutes reaction time with the addition of 50 μl of 4% KOH. The reaction products are separated from unreacted substrate after application to a C-18 octadecyl 1 ccBond column (Analytichem Int product No. 617101). An aqueous fraction is eluted with 250 μl of 0.1M KOH. Squalene is then eluted with 1.0 ml 10% ethylacetate in hexane and radioactivity determined. The difference in radioactivity in the presence and absence of the test compound is used to determine the level of inhibition. If the test compound inhibits at greater than about 70% at 25 micromolar, it is generally re-tested at 25 and 2.5 micromolar. The $IC_{50}$ (concentration which results in a 50% inhibition of squalene production), of the test compound can be determined by testing the compound at several, for example five, concentrations predicted from the two concentration results. The $IC_{50}$ can then be determined from a plot of percentage inhibition against concentration of test compound.

In general, compounds of formula I show significant inhibition in the above test at a concentration in the range of about 0.001 to 25 μM.

By way of illustration of the squalene synthase inhibitory properties of the compounds of formula I, the compound of formula I described in Example 2 below gave about 98% inhibition at 2.5 μM.

(b) Acute rat cholesterol synthesis assay.

This is an acute in vivo test in the rat to measure de novo hepatic cholesterol synthesis from exogenously administered $^{14}$C-acetate.

Female rats (35–55 g) are housed in reverse lighting conditions (red light from 0200 h–1400 h) for a period of about 2 weeks prior to test. Animals are allowed free access to chow and drinking water throughout this period. At test, animals should weigh 125–150 g.

Test compounds may be administered by oral gavage, dissolved or suspended in 0.5% polysorbate, or by ip or iv dosing. Control animals receive vehicle alone. After 1 hour the rats are injected ip with 25 μCi [2-$^{14}$C]-acetate (NEN DUPONT, specific activity, 45–60 mCi/mmol NEC-085H. or AMERSHAM specific activity, 50–60 mCi/mmol CFA 14) in a volume of 0.25 ml saline (100 μCi/ml). After a further hour, rats are terminally anaesthetised with halothane and a blood sample obtained from the abdominal vena cava.

1 ml of plasma is lyophilised and then saponified in 2 ml ethanolic KOH (1 part 33% KOH, 9 parts ethanol) at 75° C. for 2 hours. After addition of an equal quantity of water, non-saponifiable lipids are extracted with two 5 ml volumes of hexane. The hexane extracts are evaporated to dryness and the residues dissolved in ethanol to determine cholesterol specific radioactivity. $ED_{50}$ values can be determined in the standard way.

In general, compounds of formula I show activity in the range of about 0.1 to 100 mg/kg.

By way of illustration, the compound of formula I described in Example 2 gave an $ED_{50}$ of 8 mg/kg.

No overt toxicity was detected when compounds of the formula I were administered at several multiples of their minimum inhibitory dose or concentration.

As mentioned above, the compounds of the present invention are squalene synthase inhibitors and hence possess the property of inhibiting cholesterol biosynthesis. Thus the compounds of the present invention will be useful in treating diseases or medical conditions in which an inhibition of squalene synthase is desirable, for example those in which a lowering of the level of cholesterol is blood plasma is desirable. In particular, the compounds of the present invention will be useful in treating hypercholesterolemia and/or ischaemic diseases associated with atheromatous vascular degeneration such as atherosclerosis. The compounds of the present invention will also be useful in treating fungal infections.

Thus according to a further feature of the present invention there is provided a method of inhibiting squalene synthase in a warm-blooded animals (such as man) requiring such treatment, which method comprises administering to said animal an effective amount of a compound of formula I (as herein defined), or a pharmaceutically-acceptable salt thereof. In particular, the present invention provides a method of inhibiting cholesterol biosynthesis, and more particularly to a method of treating hypercholesterolemia and atheromatous vascular degeneration (such as atherosclerosis).

Thus the present invention also provides the use of a compound of formula I (as herein defined), or a pharmaceutically-acceptable salt thereof, for the manufacture of a medicament for treating diseases or medical conditions in which a lowering of the level of cholesterol in blood plasma is desirable (such as hypercholesterolemia and atherosclerosis).

When used in the treatment of diseases and medical conditions in which an inhibition of cholesterol biosynthesis is desired, for example in the treatment of hypercholesterolemia or atherosclerosis, it is envisaged that a compound of formula I (or a pharmaceutically acceptable salt thereof) will be administered orally, intravenously, or by some other medically acceptable route so that a dose in the general range of, for example, 0.01 to 50 mg per kg body weight is received. However it will be understood that the precise dose administered will necessarily vary according to the nature and severity of the disease, the age and sex of the patient being treated and the route of administration.

In general, the compounds of formula I (or a pharmaceutically-acceptable salt thereof) will usually be administered in the form of a pharmaceutical composition, that is together with a pharmaceutically acceptable diluent or carrier, and such a composition is provided as a further feature of the present invention.

A pharmaceutical composition of the present invention may be in a variety of dosage forms. For example, it may be in the form of tablets, capsules, solutions or suspensions for oral administration, in the form of a suppository for rectal administration; in the form of a sterile solution or suspension for parenteral administration such as by intravenous or intramuscular injection.

A composition may be obtained by conventional procedures using pharmaceutically acceptable diluents and carriers well known in the art. Tablets end capsules for oral administration may conveniently be formed with a coating, such as an enteric coating (for example, one based on cellulose acetate phthalate), to minimise dissolution of the active ingredient of formula I (or a pharmaceutically-acceptable salt thereof) in the stomach or to mask unpleasant taste.

The compounds of the present invention may, if desired, be administered together with (or sequentially to) one or more other pharmacological agents known to be useful in the treatment of cardiovascular disease, for example, together with agents such as HMG-CoA reductase inhibitors, bile acid seguestrants, other hypocholesterolaemic agents such as fibrates, for example gemfibrozil, and drugs for the treatment of coronary heart disease. As a further example, the compounds of the present invention may, if desired, be administered together with (or sequentially to) an angiotensin converting enzyme (ACE) inhibitor, such as captopril, lisinopril, zofenopril or enalapril.

The compounds of the present invention may also find utility as antifungal agents, and so the present invention also provides a method of treating fungal infections which comprises administration to an a warm blooded animal, such as man, in need of such treatment an effective amount of a compound of formula I, or a pharmaceutically acceptable salt thereof. When used in this way the compounds of the present invention may, in addition to the formulations mentioned above, be adapted for topical administration and such a composition is provided as a further feature of the present invention. Such compositions may be in a variety of forms, for example creams or lotions.

The invention will now be illustrated by the following non-limiting Examples in which, unless otherwise stated:

(i) evaporations were carried out by rotary evaporation in vacuo;

(ii) operations were carried out at room temperature, that is in the range 18°–26° C.;

(iii) flash column chromatography or medium pressure liquid chromatography (MPLC) was performed on silica gel (Merck Kieselgel Art.9385, obtained from E Merck, Darmstadt, Germany);

(iv) yields are given for illustration only and are not necessarily the maximum attainable by diligent process development;

(v) proton NMR spectra were normally determined at 200 MHz in a solvent of DHSOd$_6$ using tetramethylsilane (TMS) as a internal standard, and are expressed as chemical shifts (delta values) in parts per million relative to TMS using conventional abbreviations for designation of major peaks: s, singlet; m, multipier; t, triplet; br, broad; d, doublet;

(vi) all end-products were characterised by microanalysis, NMR and/or mass spectroscopy (molecular ions denoted by m/z); and (vii) conventional abbreviations are used for individual radicals and recrystallisation solvents, for example, Me=methyl, Et=ethyl, Pr=Propyl, Pr$^i$=isopropyl, Bu=butyl, Bu$^i$=isobutyl, Ph=phenyl; EtOAc=ethyl acetate, Et$_2$O=ether, MeCN=acetonitrile, MeOH=methanol, EtOH=ethanol, Pr$^i$OH=2-propanol, H$_2$O=water.

EXAMPLE 1

A mixture of 3-(4-bromophenyl)pyridine (1.17 g), 3-ethynyl-3-hydroxyquinuclidine (750 mg), bis(triphenylphosphine)-palladium (II) chloride (175 mg), copper (I) iodide (88 mg), triethylamine (5.0 ml) and dimethylformamide (10 ml) was stirred at 70° C. under an atmosphere of argon for 5 hours. The triethylamine and dimethylformamide were removed by evaporation. A 2M aqueous solution of sodium hydroxide (10 ml) was added to the residue and the mixture extracted with dichloromethane (3×10 ml). The organic extracts were combined, dried (MgSO$_4$) and evaporated to give a solid residue.

This residue was purified by flash chromatography using a mixture of 10% methanol in dichloromethane containing 1% 0.880 ammonia as eluent to give 3-[2-(4-[3-pyridyl]phenylethynyl)-3-hydroxyquinuclidine (340 mg), m.p. 189°–190° C.; microananlysis, found: C, 77.5; H, 6.5; N, 9.2%; C$_{20}$H$_{20}$N$_2$0.0.25H$_2$O requires: C, 77.8; H, 6.64; N, 9.08%; NMR (DMSO-d$_6$); 1.2–1.45(1H, m), 1.5–1.7(1H, m), 1.8–2.0(3H, m), 2.7(4H, m), 2.9(1H, d), 3.15(1H, d), 5.65(1H, s), 7.5(3H, m), 7.75(2H, d), 8.1(1H, m), 8.6(1H, m) and 8.9(1H, m); m/Z 305 (M+H).

The 3-ethynyl-3-hydroxyquinuclidine used as starting material was obtained as follows:

A solution of n-butyl lithium (100 ml of a 2M solution in pentane) was added portion-wise over a period of 20 minutes to a stirred solution of ethynyltrimethylsilane (19.6 g) in dry tetrahydrofuran (400 ml) at −70° C. The mixture was stirred for 1 hour at −70° C. A solution of 3-quinuclidone (2.4 g) in dry tetrahydrofuran (100 ml) was then added to the mixture and the mixture stirred for 1 hour at −70° C. Methanol (1 ml) was then added to the mixture and the mixture allowed to warm to room temperature. The solvents were removed by evaporation. Methanol (500 ml) and potassium carbonate (40 g) were added to the residue and the mixture was stirred for 1 hour. The solvent was removed by evaporation. The residue was triturated with water (500 ml) and the solid obtained dried in vacuo. There was thus obtained 3-ethynyl-3-hydroxy-quinuclidine as a solid, m.p. 193°–197° C.; NMR (DMSO-d$_6$): 1.5–1.3(1H, m), 1.4–1.6 (1H, m), 1.7–1.95(3H, m), 2.55–2.8(5H, m), 2.95(1H, d), 3.3(1H, d) and 5.4(1H, s); m/Z 152 (M+H).

The 3-(4-bromophenyl)pyridine used as starting material was obtained as follows:

A solution of 4-bromobenzeneboronic acid (6.0 g) in absolute ethanol (15 ml) was added slowly to a stirred mixture of a solution of 3-bromopyridine (4.7 g) in toluene (30 ml), a saturated aqueous solution of sodium carbonate (10 ml) and tetrakistriphenylphosphine palladium [0] (1.0 g) under an atmosphere of argon. The mixture was then heated to reflux and stirred at reflux under an atmosphere of argon for 6 hours. The mixture was cooled and water (50 ml) added. The resulting mixture was extracted with ethyl acetate (3×30 ml). The ethyl acetate extracts were combined, and then extracted with 2N aqueous hydrochloric acid (3×20 ml). The acidic extracts were combined, cooled by the addition of ice and basified by the addition of sodium hydroxide solution to give a pH of 9. The mixture was then extracted with ethyl acetate (3×30 ml). These ethyl acetate extracts were combined, dried ($MgSO_4$) and evaporated to afford 3-(4-bromophenyl)pyridine as a colourless oil (1.2 g); NMR ($CDCl_3$): 7.3–7.5(3H, m), 7.6(2H, d), 7.85(1H, d of t), 8.6(1H, d of d) and 8.8(1H, d).

EXAMPLE 2

A mixture of 3-ethynyl-3-hydroxyquinuclidine (516 mg), 2-(4-bromophenyl)pyridine (400 mg), bis-(triphenylphosphine)palladium (II) chloride (100 mg), copper(I) iodide (50 mg) triethylamine (15 ml) and dimethylformamide (10 ml) was stirred at 90° C. under an atmosphere of argon for 2.5 hours. The mixture was allowed to cool to room temperature, alumina (5 g) added and the solvents removed by evaporation. This pre-absorbed material was chromatographed on alumina (30 g) using a mixture of 10% ethanol in ethyl acetate as eluent. There was thus obtained a residue which was crystallised from ethanol/hexane to give 3-[2-(4-[2-pyridyl]phenyl)ethynyl]-3-hydroxyquinuclidine as a solid, m.p. 205°–206° C.; microanalysis, found: C, 77.7; H, 6.4; N, 9.0%; $C_{20}H_2ON_2O.0.25H_2O$ requires: C, 77.8; H, 6.5; N, 9.08%; NMR (DMSO-$d_6$): 1.3(1H, m), 1.6(1H, m), 1.8–2.0(3H, m), 2.7(4H, m), 2.85(1H, d), 3.1(1H, d), 5.6(1H, s), 7.4(1H, m), 7.5(2H, d), 7.85–8.05(2H, m), 8.1(1H, d) and 8.7(1H, d); m/Z 305 (M+H).

The 2-(4-bromophenyl)pyridine used as starting material was obtained using the procedure described in Example 1 for the preparation of 3-(4-bromophenyl)pyridine, but using 2-bromopyridine in place of 3-bromopyridine. There was thus obtained 2-(4-bromophenyl)pyridine as an oil, NMR ($CDCl_3$): 7.25(1H, m), 7.6(2H, d), 7.7–7.8(2H, m), 7.9(1H, d), 8.5(1H, d of d).

EXAMPLE 3

A mixture of 3-ethynyl-3-hydroxyquinuclidine (302 mg), 4-(1-imidazolyl)phenyl triflate (584 mg), bis-(triphenylphosphine)-palladium (II) chloride (140 mg), copper (I) iodide (70 mg), triethylamine (5 ml) and dimethylformamide (10 ml) was stirred at 90° C. under an atmosphere of argon for 6 hours. The mixture was evaporated and the residue purified by flash chromatography using a gradient of 10% methanol in dichloromethane containing 1% 0.880 ammonia to 15% methanol in dichloromethane containing 1% 0.880 ammonia as eluent to give a residue which was further purified by reverse phase preparative HPLC, using a mixture of 80% aqueous methanol containing 0.5% triethylamine as eluent. There was thus obtained 3-[2-(4-[1-imidazolyl]phenyl)ethynyl]-3-hydroxyquinuclidine (70 mg) as a solid, m.p. 236°–240° C.; microanalysis, found: C, 72.8; H, 6.5; N, 13.8%; $C_{18}H_{19}N_3O.0.25H_2O$ requires: C, 72.6; H, 6.55; N, 14.1%; NMR (DMSO-$d_6$): 1.2–1.4(1H,m), 1.5–1.7(1H, m), 1.8–2.02(3H, m), 2.6–2.8(4H, m), 2.85(1H,d), 3.1(1H,d), 5.65(1H,s), 7.1(1H,s), 7.5–7.6(2H,m), 7.62–7.7(2H, m), 7.8 (1H, s) and 8.3(1H, s); m/Z 294 (M+H).

The 4-(1-imidazolyl)phenyl triflate used as starting material was obtained as follows:

Triflic anhydride (2.82 g) was added dropwise to a mixture of 4-(1-imidazolyl)phenol (Aldrich Chemical Company) and triethylamine (1.1 g) in dichloromethane (30 ml). The mixture was stirred for 18 hours. The mixture was evaporated and the residue partitioned between diethyl ether and water. The organic phase was separated, washed with water, dried ($MgSO_4$) and evaporated. The residue was triturated with cyclohexane to give crude 4-(1-imidazolyl) phenyl triflate (1.7 g) as a solid, which was used without further purification; m/Z 293 (M+H).

EXAMPLE 4

A mixture of 3-ethenyl-3-hydroxyquinuclidine (673 mg), 3-(4-bromophenyl)pyridine (1.08 g), bis-(triphenylphosphine)-palladium (II) chloride (140 mg), copper (I) iodide (70 mg), and dimethylformamide (10 ml) was stirred at 130° C. under an atmosphere of argon for 4 hours. The mixture was evaporated and the residue was paritioned between aqueous 2M sodium hydroxide solution (10 ml) and dichloromethane (10 ml). The organic layer was separated, washed with dichloromethane (2×10 ml), dried ($MgSO_4$) and evaporated. The residue was crystallised from acetonitrile to give 3-[2-(4-[3-pyridyl]phenyl)ethenyl]-3-hydroxyquinuclidine (400 mg) as a solid, m.p. 195°–198° C.; microanalysis, found: C, 76.4; H, 7.2; N, 8.6%; $C_{20}H_{22}N_2O.0.5H_2O$ requires: C, 76.2; H, 7.3; N, 8.9%; NMR (DMSO-$d_6$+$CD_3COOD$): 1.7–2.15(4H, m), 2.35(1H, m), 3.15–3.4(5H, m), 3.5(1H, d), 6.7(1H, d), 6.9(1H, d), 7.5–7.8(7H, m), 8.15(1H, d); m/Z 307 (M+H).

The 3-ethenyl-3-hydroxyquinuclidine used as starting material was prepared as follows:

A mixture of 3-ethynyl-3-hydroxyquinuclidine (5.0g), palladium on calcium carbonate (5% w/w, 0.5 g) and ethanol (200 ml) was stirred under an atmosphere of hydrogen until 900 ml of hydrogen has been consumed. The mixture was filtered and evaporated to give 3-ethenyl-3-hydroxyquinuclidine (5.0 g) as an oil which gave a solid on standing and was used without further purification, m.p. 76°–80° C.; NMR(DMSO-$d_6$): 1.2(1H, m), 1.4–1.6(3H, m), 2.0(1H, m), 2.45–2.85(6H, m), 4.55(1H, s), 5.0(1H, d of d), 5.25(1H, d of d), 6.1(1H, d of d); m/z 154 (M+H).

The 3-ethynyl-3-hydroxyquinuclidine was prepared as described in Example 1.

EXAMPLE 5

A mixture of 3-[2-(4-[3-pyridyl]phenyl)ethenyl] quinuclidine (153 mg), palladium-on-charcoal (10% w/w, 25 mg) and ethanol (20 ml) was stirred under an atmosphere of hydrogen until no further hydrogen uptake occured. The mixture was filtered and the filtrate was evaporated. This residue was treated with excess of a solution of hydrogen chloride in ether to give 3-[2-(4-[3-pyridyl]phenyl)ethyl]-3-hydroxyrquinuclidine dihydrochloride as a solid (110 mg), m.p. 259°–261° C.; microanalysis, found: C, 60.7; H, 7.0; N, 6.7%; $C_{20}H_{24}NO_2.2HCl$ requires C, 60.1; H, 7.0; N, 7.0%; NMR (DMSO-$d_6$): 1.6–2.1(6H, m), 2.3(1H, m), 2.7(2H, m), 3.0–3.3(6H, m), 7.45(2H, d), 7.8(2H, d), 8.0(1H, m), 8.65 (1H, d), 8.8(1H, d) and 9.2(1H, m); m/Z 309 (M+H).

EXAMPLE 6

An ice-cooled solution of aqueous 3M hydrochloric acid (7.0 ml) in acetone (21.0 ml) was added to 3-hydroxy-3-[4-(3-pyridyl)phenoxymethyl]quinuclidine borane complex (1.4 g). The latter dissolved immediately and the resulting colourless solution was stirred at 5° C. for 1 hour during which a colourless precipitate formed. This solid was collected by filtration, washed with acetone and dried to afford crude product (1.02 g) which was recrystallised from ethanol (10 ml) to give 3-hydroxy-3-[4-(3-pyridyl)phenoxymethyl] quinuclidine dihydrochloride as a colourless solid (0.75 g), m.p. 263°–265° C.; microanalysis, found: C, 58.3; H, 6.7; N, 6.8%; $C_{19}H_{22}N_2O_2.2HCl.0.4H_2O.0.3EtOH$ requires: C, 58.2; H, 6.6; N, 6.9%; NMR (DMSO-$d_6$): 1.58–1.8(1H, m), 1.75–2.0(2H, m), 2.21(1H, s), 2.95–3.4(6H, m), 4.15(2H, s), 7.16 and 7.85(4H, 2d), 8.02(1H,m), 8.77(2H, d), 9.18(1H, s), and 10.73(1H, s); m/z 311 (M+H).

The 3-hydroxy-3-[4-(3-pyridyl)phenoxymethyl] quinuclidine borane complex used as starting material was obtained as follows.

A solution of borane-tetrahydrofuran complex (135 ml of a 1M solution in tetrahydrofuran) was added portionwise over a period of 30 minutes to a stirred solution of 3-quinuclidinone (16.9 g) in dry tetrahydrofuran (300 ml) at −70° C. The mixture was stirred at −70° C. for 30 minutes. Water (20 ml) was added to the reaction mixture at −70° C. The solvent was removed by evaporation. A saturated solution of brine (250 ml) was added to the residue and the mixture was basified by addition of solid sodium carbonate. The mixture was extracted with dichloromethane (4×100 ml). The dichloromethane extracts were combined, silica gel (Merck 9385, 60 g) was added and the mixture was evaporated to give a free flowing powder. This pre-absorbed material on silica gel was purified by flash column chromatography on a further portion of silica gel using a mixture of 25% ethyl acetate/pentane as eluent to give 3-quinuclidinone borane complex (17.0 g) as a colourless solid, m.p. 162°–164° C.; NMR (CDCl$_3$): 0.7–2.3(3H, br), 2.0–2.3(4H, m), 2.7(1H, m), 3.0–3.4(4H, m) and 3.5(2H, s).

Powdered trimethyl sulphoxonium iodide (24.4 g) was added portionwise to a stirred, ice-cooled, suspension of sodium hydride (60% w/w dispersion in mineral oil, 4.4 g; the oil was removed by washing the solid with petroleum ether) in dry dimethylformamide (140 ml) under an atmosphere of argon whilst maintaining the temperature at 10° to 15° C. The mixture was allowed to warm to room temperature. Solid 3-quinuclidinone borane complex (15.5 g) was added to the stirred mixture whilst maintaining the temperature at 25° to 30° C. using an ice-bath. The mixture was then stirred at room temperature for 16 hours.
The mixture was poured into water (1400 ml) and the mixture was extracted with ethyl acetate (4×400 ml).

The ethyl acetate extracts were combined, washed with water (3×300 ml), dried (Na$_2$SO$_4$) and evaporated. The residue was purified by flash column chromatography on silica gel using dichloromethane as eluent to give 3-methylenequinuclidine oxide borane complex (13.8 g) as a colourless solid, m.p. 74°–77° C.; microanalysis, found: C, 63.1; H, 10.6; N, 9.2%; $C_8H_{16}BNO$ requires: C, 62.8; H, 10.5; N, 9.2%; NMR (CDCl$_3$): 0.6–2.3(3H, br), 1.6(1H, m), 1.7–1.9(1H, m), 1.9–2.0(2H, m), 2.1–2.3(1H, m), 2.8(2H, q) and 2.9–3.4(6H, m); m/z 152 (M−H).

Solid potassium carbonate (2.21 g) was added to a solution of 4-(3-pyridyl)phenol (1.37 g) and 3-methylenequinuclidine oxide borane complex (1.22 g) in dry dimethylformamide (10 ml) under an atmosphere of argon. The mixture was stirred for 64 hours at room temperature followed by 3 hours at 70° C. The mixture was poured into water (100 ml) and the mixture extracted with ethyl acetate (3×70 ml, 1×40 ml). The ethyl acetate extracts were combined, washed successively with water (3×60 ml) and aqueous 2M sodium hydroxide solution (1×60 ml, 1×30 ml) and then extracted with aqueous 2M hydrochloric acid solution (2×50 ml, 1×30 ml). The acidic aqueous extracts were combined, washed with ethyl acetate (2×50 ml) and then basified by addition of solid sodium carbonate to precipitate an oil which was extracted with ethyl acetate (3×70 ml). The ethyl acetate extracts were combined, dried (Na$_2$SO$_4$) and evaporated to give a yellow oil/foam (2.3 g) which, on trituration with ethyl acetate (10 ml), afforded a pale yellow solid (1.8 g). This solid was purified by flash chromatography using an eluent of ethyl acetate. There was thus obtained 3-hydroxy-3-[4-(3-pyridyl)phenoxymethyl] quinuclidine borane complex as a colourless solid (1.56 g), m.p. 157°–159° C.; microanalysis, found: C, 70.3; H, 8.0; N, 8.6; $C_{19}H_{25}BN_2O_2$ requires: C, 70.4; H, 7.8; N, 8.6%; NMR (DMSO-$d_6$): 0.5–2.5(3H,br), 1.53–1.75(1H, m), 1.73–1.95 (2H, m), 2.23–2.48(2H, m), 2.8–3.3(6H, m), 3.33(1H, br s), 3.93–4.12(2H, q), 7.00 and 7.5(4H, 2d), 7.35(1H, m), 7.83 (1H, m), 8.55(1H, d), 8.77(1H, s); m/z 323 (M−H).

EXAMPLES 7–32

Using a procedure similar to that described in Example 1, the following compounds of formula I, wherein Ar$^2$ has the indicated values were prepared from the corresponding compounds of formula 2 (in which Z is bromo unless stated otherwise), with purification procedures and exceptions as noted. Where the compounds of formula 2 are not commercially available preparative details are given.

EXAMPLE 7

Ar$^2$=1-pyrrolyl

Purified by flash column chromatography on silica gel using 10% methanol in dichloromethane containing 1% ammonia (density, 0.88 g/cm$^3$) as eluent to give the title compound as a solid, m.p. 211°–213° C.; NMR: 1.2–1.4 (1H,m), 1.5–1.7(1H,m), 1.8–2.0(3H,m), 2.6–2.8(4H,m), 2.8–2.94(1H,d), 3.05–3.15(1H,d), 5.61(1H,s), 6.27(2H,m) and 7.33–7.65(6H,m).

EXAMPLE 8

Ar$^2$=5-methyl-1,2,4-oxadiazol-3-yl

Purified by crystallisation from acetonitrile to give the title compound as a solid, m.p. 214°–215° C.; NMR: 1.2–1.4 (1H,m), 1.5–1.7(1H,m), 1.8–2.0(3H,m), 2.6–2.8(4H,m), 2.66(3H,s), 2.8–2.9(1H,d), 3.05–3.15(1H,d), 5.68(1H,s), 7.59(2H,d) and 7.99(2H,d).

The compound of formula 2 (Z=iodo) was prepared as follows.

A mixture of 4-iodobenzonitrile (7.69 g), anhydrous sodium carbonate (6.25 g), hydroxylamine hydrochloride (8.74 g), in water (60 ml) and sufficient ethanol to maintain a clear solution, was heated at 90°–100° C. for 4 hours. The reaction mixture was cooled to ambient temperature and evaporated until a precipitate formed. The solid was collected by filtration, washed with water and recrystallised from acetonitrile to give 4-iodobenzamidoxime (5.97 g), m.p. 155°–161° C.; microanalysis, found: C, 31.4; H, 2.7; N, 10.2%; $C_7H_7IN_2O$ 0.2H$_2$O requires: C, 31.6; H, 2.81; R, 10.5%; NMR: 5.82(2H,s), 7.46(2H,d), 7.73(2H,d), 9.69(1H, s); m/z 263(M+H).

Acetyl chloride (1.62 ml) was added to a solution of 4-iodobenzamidoxime (5.24 g) in pyridine (35 ml) at ambient temperature. The reaction mixture was heated at reflux for 3 hours. The mixture was cooled to ambient temperature, evaporated and ice-water was added to the residue. The solid was collected by filtration, washed with water and recrystallised from acetonitrile to give 3-(4-iodophenyl)-5-methyl-1,2,4-oxadiazole (4.43 g), m.p. 121°–122° C.; microanalysis found: C, 37.6; H, 2.4; N, 9.7%; $C_9H_7IN_2O$ requires: C, 37.8; H, 2.47; N, 9.79%; NMR: 2.66(3H,s), 7.77(2H,dd) and 7.94(2H,dd); m/z 287(M+H).

EXAMPLE 9

$Ar^2$=4-pyridyl

Purified by flash column chromatography on silica gel using 10% methanol in dichloromethane containing 1% ammonia (density, 0.88 g/cm³) as eluent, followed by recrystallisation from acetonitrile, to give the title compound as a solid, m.p. 201°–202° C.; NMR: 1.2–1.4(1H,m), 1.5–1.7(1H,m), 1.8–2.0(3H,m), 2.6–2.8(4H,m), 2.8–2.9(1H, d), 3.05–3.15(1H,d), 5.63(1H,s), 7.55(2H,d), 7.73(2H,d), 7.83(2H,d) and 8.64(2H,d).

The compound of formula 2 used as starting material was prepared as follows.

A solution of 4-bromobenzeneboronic acid (2 g) in absolute ethanol (10 ml) was added slowly to a stirred mixture of 4-bromopyridine hydrochloride (1.96 g) in toluene (10 ml), 2M aqueous sodium carbonate solution (25 ml) and tetrakistriphenylphosphine palladium [0] (345 mg) under an atmosphere of argon. The mixture was heated to reflux and stirred at reflux for 3 hours. The mixture was cooled to ambient temperature and water (50 ml) was added. The resulting mixture was extracted with ethyl acetate (3×20 ml). The ethyl acetate extracts were combined and extracted with 2N aqueous hydrochloric acid. The acidic extract was cooled and basified by the addition of aqueous sodium hydroxide solution to give a pH of 9. The mixture was then extracted with ethyl acetate (5×50 ml). The ethyl acetate extracts were combined, dried (MgSO₄) and evaporated to give 4-(pyrid-4-yl)bromobenzene as a solid (0.71 g), m.p. 123°–124° C.; microanalysis, found: C, 56.4; H, 3.4; N, 5.9%; $C_{11}H_8BrN$ requires: C, 56.4; H, 3.4; N, 6.0%; m/z 234(M+H).

EXAMPLE 10

$Ar^2$=5-pyrimidinyl

Purified by flash chromatography on silica gel using 10% methanol in dichloromethane containing 1% ammonia (density, 0.88 g/cm³) as eluent, followed by recrystallisation from acetonitrile, to give the title compound as a solid, m.p. 218°–219° C.; NMR: 1.1–1.3(1H,m), 1.38–1.57(1H,m), 1.66–1.9(3H,m), 2.5–2.65(4H,m), 2.66–2.8(1H,d), 2.94–3.05(1H,d), 5.54(1H,s), 7.42(2H,d), 7.70(2H,d) and 9.01–9.06(3H,m).

The compound of formula 2, 4-(pyrimidin-5-yl)bromobenzene, used as starting material was prepared using the method described in Example 9 for the preparation of 4-(pyrid-4-yl)bromobenzene but using 5-bromopyrimidine as starting material in place of 4-bromopyridine. There was thus obtained 4-(pyrimidin-5-yl)bromobenzene as a solid, m.p. 138°–140° C.; NMR: 7.69–7.83(4H,m), 9.15(2H,s) and 9.21(1H,s); m/z 235(M+H).

EXAMPLE 11

$Ar^2$=3-methyl-1,2,4-oxadiazol-5-yl

Purified by crystallisation from acetonitrile to give the title compound as a solid, m.p. 198°–199° C.; NMR: 1.2–1.4 (1H,m), 1.5–1.7(1H,m), 1.8–2.0(3H,m), 2.43(3H,s), 2.6–2.8 (4H,m), 2.8–2.9(1H,d), 3.05–3.15(1H,d), 5.72(1H,s), 7.64 (2H,d) and 8.07(2H,d).

The compound of formula 2 (Z=iodo) was prepared as follows.

Acetamidoxime hydrochloride (1.5 g) was added portionwise to an ice-cooled suspension of sodium hydride (1.18 g of a 60% dispersion in oil) in dry tetrahydrofuran (40 ml) under an atmosphere of argon. Molecular sieve type 4A (8–12 mesh) were added followed by a solution of ethyl 4-iodobenzoate (3.73 g) in tetrahydrofuran (10 ml). The mixture was heated at 65° C. for 3 hours. The mixture was cooled to ambient temperature and partitioned between ethyl acetate and water. The organic extract was separated, washed with saturated brine, dried (MgSO₄) and evaporated. The residue was purified by flash column chromatgraphy on silica gel using a 70:30 (v/v) mixture of ethyl acetate/hexane as eluent to give 3-methyl-5-(4-iodophenyl)-1,2,4-oxadiazole as a solid (1.12 g), m.p. 136°–7° C.; microanalysis, found: C, 38.2; H, 2.5; H, 9.5%; $C_9H_7IN_2O$ requires: C, 37.8; H, 2.47; N, 9.79%; NMR: 2.41(3H,s), 7.84(2H,d) and 8.02(2H,d); m/z 287(M+H).

EXAMPLE 12

$Ar^2$=5-ethyl-1,2,4-oxadiazol-3-yl

Purified by flash column chromatography on silica gel using 10% methanol in dichloromethane containing 1% ammonia (density, 0.88 g/cm³) as eluent, followed by recrystallisation from acetonitrile to give the title compound as a solid, m.p. 188°–189° C.; NMR: 1.2–1.4(1H,m), 1.34 (3H,t), 1.5–1.7(1H,m), 1.8–2.0(3H,m), 2.6–2.8(4H,m), 2.8–2.9(1H,d), 3.02(2H,q), 3.05–3.15(1H,d), 5.66(1H,s), 7.59(2H,d) and 8.00(2H,d).

The compound of formula 2 (Z=iodo), 3-(4-iodophenyl)-5-ethyl-1,2,4-oxadiazole, used as starting material was prepared by the method described in Example 8 for the preparation of 3-(4-iodophenyl)-5-methyl-1,2,4-oxadiazole but using propionyl chloride in place of acetyl chloride. There was thus obtained 3-(4-iodophenyl)-5-ethyl-1,2,4-oxadiazole as an oil; NMR: 1.35(3H,t), 3.01(2H,q), 7.76 (2H,d), 7.94(2H,d); m/z 301(M+H).

EXAMPLE 13

$Ar^2$=5-isopropyl-1,2,4-oxadiazol-3-yl

Purified by crystallisation from methanol to give the title compound as a solid, m.p. 201°–202° C.; NMR: 1.35–1.90 (2H,m), 1.53(6H,d), 1.90–2.24(3H,m), 2.75–2.95(4H,m), 2.85–3.08(1H,d), 3.18–3.31(1H,d), 3.35–3.63(1H,m), 5.80 (1H,s), 7.72(2H,d) and 8.14(2H,d).

The compound of formula 2 (Z=iodo), 3-(4-iodophenyl)-5-isopropyl-1,2,4-oxadiazole, used as starting material was prepared by the method described in Example 8 for the preparation of 3-(4-iodophenyl)-5-methyl-1,2,4-oxadiazole but using isobutyryl chloride in place of acetyl chloride. There was thus obtained 3-(4-iodophenyl)-5-isopropyl-1,2, 4-oxadiazole was an oil; microanalysis, found: C, 42.4; H, 3.5; N, 8.5%; $C_{11}H_{11}IN_2O$ requires: C, 42.1; H, 3.53; N, 8.92%; NMR(CDCl₃): 1.45(6H,d), 3.17–3.40(1H,m) and 7.81(4H,s); m/z 315(M+H).

EXAMPLE 14

$Ar^2$=2-benz-1,3-thiazolyl

Solid precipitated after mixture basified with sodium hydroxide solution. The solid was collected by filtration, washed with dichloromethane followed by water and recrystallised from methoxyethanol to give the title compound as a solid, m.p. 248°–249° C.; NMR: 1.3–1.5(1H,m), 1.6–1.8 (1H,m), 1.9–2.1(3H,m), 2.7–2.9(4H,t), 2.9–3.05(1H,d), 3.15–3.3(1H,d), 5.4(1H,m), 7.4–7.6(4H,m) and 8.0–8.2(4H,m).

The compound of formula 2 (Z=Br) was prepared by the method of JACS., 55, (1971), 309.

EXAMPLE 15

Ar$^2$=2-benz-1,3-oxazolyl

Solid precipiated after mixture basified with sodium hydroxide solution. The solid was collected by filtration, washed with dichloromethane followed by water and recrystallised from m-ethoxyethanol to give the title compound as a solid, m.p. 277°–278° C.; NMR: 1.25–1.45(1H,m), 1.55–1.8(1H,m), 1.8–2.1(3H,m), 2.6–3.25(6H,m), 5.7(1H, s), 7.3–7.5(2H,m), 7.55–7.7(2H,d), 7.7–7.9(2H,m) and 8.1–8.3(2H,d).

The compound of formula 2 (Z=Br) was prepared by the method of Helv. Chim. Acta., 63, (1980), 418.

EXAMPLE 16

Ar$^2$=1-methyl-indol-2-yl

Solid precipitated after mixture basified with sodium hydroxide solution. The solid was collected by filtration, washed with dichloromethane followed by water and recrystallised from methoxyethanol to give the title compound as a solid, m.p. 238°–239° C.; NMR: 1.3–1.5(1H,m), 1.6–1.8 (1H,m), 1.85–2.15(3H,m), 2.6–3.6(6H,m), 3.75 (3H,s), 5.7 (1H,s), 6.6(1H,s), 7.0–7.4(2H, m) and 7.4–7.7(4H,m).

The compound of formula 2 was prepared as follows.

Potassium tert-butoxide (1.23 g) was added to a solution of 2-(4-bromophenyl)indole (2.72 g) in dimethylformamide (40 ml). Iodomethane (1.25 ml) was added and the reaction mixture stirred at ambient temperature for 18 hours. The reaction mixture was added to water. This solid was collected by filtration and purified by vacuum chromatography on silica gel (Merck Art. 7736) using 5% ethyl acetate/ hexane as eluent to give 2-(4-bromophenyl)-1-methylindole (1.625 g) as a solid, m.p. 114°–115° C.

EXAMPLE 17

Ar$^2$=2-quinolyl

Solid precipiated after mixture basified with sodium hydroxide solution. The solid was collected by filtration, washed with dichloromethane followed by water and recrystallised from methoxyethanol to give the title compound as a solid, m.p. 246°–248° C.; NMR: 1.2–1.4(1H,m), 1.5–1.8 (1H,m), 1.8–2.1(3H,m), 2.6–3.15(5H,m), 3.2–3.3(1H,d), 5.7 (1H,s), 7.5–7.7(3H,m), 7.7–7.9(1H,t), 7.9–8.1(2H,m), 8.1–8.2(1H,d), 8.2–8.4(2H,d) and 8.4–8.5(1H,d).

The compound of formula 2, 2-(4-bromophenyl) quinoline, used as starting material was prepared using the method of Suzuki et al, Sn. Comm., 11, (1981), 513 as a solid, m.p. 115° C.

EXAMPLE 18

Ar$^2$=2-indolyl

Solid precipiated after mixture basified with sodium hydroxide solution. The solid was collected by filtration, washed with dichloromethane followed by water and recrystallised from aqueous dimethylformamide to give the title compound as a solid, m.p. 267°–272° C.; NMR: 1.2–1.45 (1H,m), 1.5–1.8(1H,m), 1.8–2.1(3H,m), 2.6–3.5(6H,m), 5.6 (1H,s), 6.9–7.2(3H,m), 7.3–7.6(4H,m) and 7.7–7.9(2H,d).

The compound of formula 2, 2-(4-bromophenyl)indole, used as starting material was prepared from 4-bromoacetophenone using the method described in J. Med. Chem., 7, (1964), 737 as a solid, m.p. 210°–212° C.

EXAMPLE 19

Ar$^2$=5-methoxy-1-methyl-pyrazol-3-yl

Extracted with ethyl acetate in place of dichoromethane. Crystallised from acetonitrile to give the title compound as a solid, m.p. 194°–196° C.; NMR: 1.2–1.4(1H,m), 1.5–1.7 (1H,m), 1.8–2.0(3H,m), 2.6–2.8(4H,t), 2.8–2.9(1H,d), 3.0–3.1(1H,d), 3.6(3H,s), 3.9(3H,s), 5.6(1H,s), 6.2(1H,s), 7.4–7.5(2H,d) and 7.7–7.8(2H,d).

The compound of formula 2, 3-(4-bromophenyl)-5-methoxy-1-methylpyrazole, used as starting material was prepared as follows.

A mixture of 3-(4-bromophenyl)-5-hydroxy-1-methylpyrazole (2.5 g), acetone (200 ml), potassium carbonate (1.6 g) and methyl iodide (1.4 g) was heated at reflux for 2 hours. The mixture was filtered and the filtrate was evaporated. The residue was purified by flash column chromatography on silica gel using 10% ethyl acetate/toluene as eluent to give 3-(4-bromophenyl)-5-methoxy-1-methypyrazole (590 mg) as a solid, m.p. 71°–73° C.; NMR: 3.6(3H,s), 3.9(3H,s), 6.2(1H,s), 7.5–7.6(2H,d) and 7.6–7.7 (2H,d).

The 3-(4-bromophenyl)-5-hydroxy-5-hydroxy-1-methylpyrazole was prepared using the method of Veibel et al., Acta. Chem. Scand., 8, (1954) 774 but using ethyl 4-bromobenzoyl acetate as starting material. There was thus obtained 3-(4-bromophenyl)-5-hydroxy-1-methylpyrazole (73% yield) as a solid, m.p. 196°–199° C.; NMR: 3.6(3H,s), 5.8(1H,s) and 7.5–7.7(4H,dd).

EXAMPLE 20

Ar$^2$=5-isoxazolyl

Purified by flash column chromagraphy on silica gel using 10% methanol in dichloromethane containing 1% ammonia (density, 0.88 g/cm$^3$) as eluent, followed by recrystallisation from acetonitrile to give the title compound as a solid, m.p. 175°–178° C.; NMR: 1.2–1.4(1H,m), 1.5–1.7(1H,m), 1.8–2.0(3H,m), 2.6–2.8(4H,m), 2.8–2.9(1H,d), 3.03–3.15 (1H,d), 5.68(1H,s), 7.06(1H,d), 7.55(2H,d), 7.86(2H,d) and 8.65(1H,d).

The compound of formula 2 used as starting material was prepared as follows.

A solution of 4-iodoacetophenone (6.15 g) in N,N-dimethylformamide dimethyl acetal (6.5 ml) was heated at reflux for 8 hours. The reaction mixture was evaporated and the solid residue was recrystallised from acetonitrile to give 1-(4-iodophenyl)-3-dimethylamino-2-propen-1-one (4.38 g), as a solid, m.p. 117°–118° C.; NMR(CDCl$_3$): 2.60–3.50 (6H,br.d), 5.64(1H,d), 7.62(2H,d), 7.77(2H,d) and 7.80(1H, d), m/z 302(M+H). A mixture of 1-(4-iodophenyl)-3-dimethylamino-2-propen-1-one (3.0 g) and hydroxylamine hydrochloride (0.73 g) in 1:1 dioxane/water (30 ml) was stirred at ambient temperature for 48 hours. Addition of water gave a solid which was collected by filtration, washed with water, and purified by flash column chromagatography on silica gel using 1:1 (v/v) ethyl acetate/pentane as eluent. There was thus obtained 5-(4-iodophenyl)-isoxazole (0.6 g); microanalysis found: C, 39.4; H, 2.3; N, 4.8%; C$_9$H$_6$INO requires: C, 39.9; H, 2.23; N, 5.17%; NMR(CDCl$_3$): 6.54 (1H,d), 7.52(2H,d), 7.83(2H,d) and 8.28(1H,d); m/e 272(M+H).

EXAMPLE 21

Ar²=5-methyl-1,3-oxazol-2-yl

Purified by flash column chromatography on silica gel using a mixture of 15% methanol in dichloromethane containing 1% ammonia (density, 0.88 g/cm³) as eluent, followed by recrystallisation from acetonitrile to give the title compound as a solid, m.p. 175°–176° C.; NMR: 1.2–1.4 (1H,m), 1.5–1.7(1H,m), 1.8–2.0(3H,m), 2.38(3H,s), 2.6–2.8 (4H,m), 2.8–2.9(1H,d), 3.05–3.15(1H,d), 5.64(1H,s), 7.01 (1H,d), 7.52(2H,d) and 7.90(2H,d).

The compound of formula 2 used as starting material was prepared as follows.

A solution of propargylamine (3.55 g) in ethyl acetate (25 ml) was added over a period of 15 minutes to a stirred mixture of 4-bromobenzoyl chloride (14.2 g) and sodium carbonate (10.6 g) in ethyl acetate (100 ml) at ambient temperature. The mixture was heated at reflux for 1 hour. The mixture was cooled to ambient temperature and water (200 ml) was added. The mixture extracted with ethyl acetate (2×100 ml). The ethyl acetate extracts were combined, washed with saturated aqueous sodium bicarbonate solution, saturated with brine, dried (MgSO₄) and evaporated. The solid residue was recrystallised from ethyl acetate to give 4-bromobenzoyl propargyl amide (8.9 g), m.p. 281°–288° C.; NMR: 3.10(1H,m), 4.05(2H,m), 7.69(2H,m), 7.80(2H,m), 9.0(1H,m); m/z 238(M+H).

Mercuric acetate (40 mg) was added to a stirred suspension of 4-bromobenzoyl propargyl amide (3.57 g) in acetic acid (30 ml) and the mixture heated at reflux for 1.25 hours. The mixture was cooled to ambient temperature, evaporated and the residue azeotroped with toluene to give a solid which was purified by column chromatography on silica gel (Merck 7734) using 30% ethyl acetate/hexane as eluent. There was thus obtained 2-(4-bromophenyl)-5-methyloxazole (2.75 g), m.p. 66°–68° C.; NMR(CDCl₃): 2.40(3H,s); 6.81(1H,d), 7.52(2H,m) and 7.82(2H,m); m/z 238(M+H).

EXAMPLE 22

Ar²=5-ethoxycarbonyl-1,2,4-oxadiazol-3-yl

Purified by crystallisation from acetonitrile to give the title compound as a solid, m.p. 153°–154° C.; NMR: 1.2–1.4 (1H,m), 1.37(3H,t), 1.5–1.7(1H,m), 1.75–2.05(3H,m), 2.55–3.20(6H,br m), 4.47(2H,q), 5.68(1H,s), 7.6(2H, d of d) and 8.03(2H, d of d).

The compound of formula 2 (Z=iodo), 5-ethoxycarbonyl-3-(4-iodophenyl)-1,2,4-oxadiazole, used as starting material, was prepared by the method described in Example 8 for the preparation of 3-(4-iodophenyl)-5-methyl-1,2,4-oxadiazole but using ethyl oxalyl chloride in place of acetyl chloride. There was thus obtained 5-ethoxycarbonyl-3-(4-iodophenyl)-1,2,4-oxadiazole as a solid, which was recrystallised from acetonitrile, m.p. 107°–108° C.; microanalysis found: C, 38.3; H, 2.6; N, 7.9%; $C_{11}H_9IN_2O_3$ requires: C, 38.4; H, 2.64; N, 8.14%; NMR(CDCl₃): 1.50(3H,t), 4.58 (2H,q) and 7.89(4H,s); m/z 345(M+H).

EXAMPLE 23

Ar²=5-methyl-1,3,4-oxadizol-2-yl

Purified by flash column chromatography on silica gel using 15% methanol in dichloromethane containing 1% ammonia (density, 0.88 g/cm³) as eluent, followed by recrystallisation from acetonitrile, to the title compound as a solid, m.p. 217°–218° C.; NMR: 1.2–1.4(1H,m), 1.5–1.7 (1H,m), 1.8–2.0(3H,m), 2.58(3H,s), 2.6–2.8(4H,m), 2.8–2.9 (1H,d), 3.05–3.15(1H,d), 5.67(1H,s), 7.60(2H,d) and 7.95 (2H,d).

The compound of formula 2 2-(4-bromophenyl)-5-methyl-1,3,4-oxadiazole, used as starting material was prepared using the method described in Example 32 for the preparation of 2-(4-bromophenyl)-5-ethyl-1,3,4-oxadiazole but using triethylorthoacetate in place of triethylorthopropionate. There was thus obtained 2-(4-bromophenyl)-5-methyl-1,3,4-oxadiazole as a solid m.p. 116°–117° C.; microanalysis found: C, 45.1; H, 2.8; N, 11.6%; $C_9H_7BrN_2O$ requires: C, 45.2; H, 2.95; N, 11.7%; NMR(CDCl₃): 2.63 (3H,s), 7.65(2H,d) and 7.90(2H,d); m/z 239(M+H).

EXAMPLE 24

Ar²=5-methoxy-3-methylpyrazol-1-yl

Aqueous sodium hydroxide solution (10 ml) was added to the reaction mixture and the mixture extracted with diethyl ether. The organic extracts were dried (MgSO₄) and evaporated to give a solid residue which was recrystallised from acetonitrile to give the title compound as a solid, m.p. 152°–154° C.; NMR: 1.2–1.4(1H,m), 1.5–1.7(1H,m), 1.8–2.0(3H,m), 2.15(3H,s), 2.6–2.75(4H,t), 2.75–2.9(1H,d), 3.0–3.15(1H,d), 3.9(3H,s), 5.6(1H,s), 6.7(1H,s), 7.4–7.5 (2H,d) and 7.6–7.7(2H,d).

The compound of formula 2, 1-(4-bromophenyl)-5-methoxy-3-methylpyrazole, used as starting material was prepared as follows.

A mixture of 1-(4-bromophenyl)-3-methyl-pyrazol-5-one (3.6 g), 10N aqueous sodium hydroxide solution (1.57 ml), methanol (5 ml) and dimethylsulphate (1.4 ml) was heated at reflux for 2 hours. The crude product was purified by vacuum flash chromatography on silica gel (Merck Art 7736) using dichloromethane as eluent to give 1-(4-bromophenyl)-5-methoxy-3-methylpyrazole (21% yield) as a solid, m.p. 67°–68° C.; NMR: 2.9(3H,s), 3.4(3H,s), 5.5 (1H,s) and 7.4–7.5(2H,d).

EXAMPLE 25

Ar²=2-methyl-5-hydroxypyrid-6-yl

Purified by flash column chromatography on silica gel using 10% methanol in dichloromethane containing 1% ammonia (density, 0.88 g/cm³) as eluent to give the title compound as a solid, m.p. 253°–256° C.; NMR: 1.25–1.45 (1H,m), 1.55–1.75(1H,m), 1.8–2.03(3H,m), 2.4(3H,s), 2.65–2.8(4H,m), 2.85–2.92(1H,d), 3.08–3.15(1H,d), 5.67 (1H,br), 7.03–7.08(1H,d), 7.2–7.25(1H,d), 7.4–7.48(2H,d), 8.02–8.1(2H,d) and 9.97(1H,br).

The compound of formula 2 used as starting material was prepared as follows.

A solution of 4-bromobenzeneboronic acid (2.0 g) in ethanol (10 ml) was added over a period of 15 minutes to a stirred mixture of 6-iodo-2-picolin-5-ol (2.35 g), saturated aqueous sodium carbonate solution (5.0 ml), tetrakis (triphenylphosphine)palladium [0] (280 mg) and toluene (10 ml) under an atmosphere of argon. The mixture was stirred at reflux for 6 hours. The mixture was evaporated and the residue was treated with water (20 ml). The mixture was filtered and the yellow solid collected was purified by flash column chromatography on alumina (1CN Biomedicals Alumina N32-63) using 50% n-pentane/ethyl. acetate as eluent to give 2-(4-bromophenyl)-3-hydroxy-6-methylpyridine (600 mg), m.p. 196°–199° C.; NMR: 2.42(3H,s), 7.09(1H, d), 7.25(1H,d), 7.62(2H,d), 8.02(2H,d), 9.98(1H,s); m/z 264 & 266 (M+H).

EXAMPLE 26

$Ar^2$=2-methoxypyrid-5-yl

Purified by flash column chromatography on silica gel using 10% methanol in ethyl acetate containing 1% ammonia (density, 0.88 g/cm$^3$) as eluent, followed by recrystallisation from acetonitrile, to give the title compound as a solid, m.p. 193°–195° C.; NMR: 1.2–1.45(1H,m), 1.55–1.75 (1H,m), 1.85–2.03(3H,m), 2.65–2.8(4H,m), 2.85–2.92(1H, d), 3.08–3.15(1H,d), 3.9(3H,s), 5.67(1H,br), 6.89–6.95(1H, d), 7.45–7.53(2H,d), 7.63–7.71(2H,d), 8.0–8.08(1H, d of d) and 8.5(1H,d).

The compound of formula 2 was prepared as follows.

Sodium hydride (2.0 g of a 60% dispersion in mineral oil) was added portionwise to methanol (30 ml) with stirring and cooling with an ice-bath. 2,5-Dibromopyridine (2.37 g) was added to the mixture and the mixture stirred at reflux for 16 hours. The methanol was removed by evaporation. Water (15 ml) was added to the residue and the mixture was extracted with dichloromethane (3×15 ml). The organic extracts were combined, dried (MgSO$_4$) and evaporated to give 5-bromo-2-methoxypyridine (2.0 g) as an oil. NMR: 3.85(3H,s), 6.83(1H,d), 7.9(1H,dd) and 8.3(1H,d).

The 5-bromo-2-methoxypyridine was reacted with 4-bromobenzeneboronic acid using the procedure described in Example 25 for the preparation of the compound of formula 2. The product was purified by flash column chromatography on silica gel using a gradient of n-pentane to 3% ethyl acetate in n-pentane to give 5-(4-bromophenyl)-2-methoxypyridine as an oil (0.56 g), NMR: 3.9(3H,s), 6.9 (1H,d), 7.61(4H,s), 8.0(1H,dd) and 8.5(1H,d).

EXAMPLE 27

$Ar^2$=3-ethoxycarbonylpyrid-5-yl

Purified by flash column chromatography on silica gel using 10% methanol in dichloromethane containing 1% ammonia (density, 0.88 g/cm$^3$) as eluent to give the title compound as a solid, m.p. 162°–165° C.; NMR: 1.39(3H,t), 1.6–1.8(1H,m), 1.8–2.0(1H,m), 2.08–2.3(3H,m), 3.02–3.2 (4H,m), 3.22(1H,d), 3.5(1H,d), 4.41(2H,q), 5.67(1H,br), 7.5–7.6(2H,d), 7.8–7.9(2H,d), 8.48(1H,t) and 9.09(2H,d).

The compound of formula 2 was prepared using the method described in Example 25 for the preparation of the compound of formula 2 but using ethyl-5-bromonicotinate (1.15 g) in place of 6-iodo-2-picolin-5-ol. There was thus obtained, after trituration with n-pentane, ethyl-5-(4-bromophenyl)nicotrinate (1.0 g) as a solid, m.p. 72°–76° C.; NMR: 1.37(3H,t), 4.4(2H,q), 7.75(4H,m), 8.45(1H,t), 9.1 (2H,d); m/z 306 and 308(M+H).

EXAMPLE 28

$Ar^2$=2-ethylpyrid-5-yl

Purified by flash column chromatography on silica gel using a gradient of 5% methanol in dichloromethane containing 1% ammonia (density, 0.88 g/cm$^3$) to 10% methanol in dichloromethane containing 1% ammonia (density, 0.88 g/cm$^3$) as eluent to give the title compound as a solid, m.p. 203°–206° C.; NMR: 1.2–1.3(3H,t), 1.2–1.45(1H,m), 1.55–1.75(1H,m), 1.85–2.03(3H,m), 2.65–2.8(4H,m), 2.75–2.85(2H,q), 2.85–2.92(1H,d), 3.08–3.15(1H,d), 5.67 (1H,br), 7.31–7.4(1H,d), 7.48–7.56(2H,d), 7.68–7.76(2H,d), 7.97–8.04(1H, d of d) and 8.8(1H,d).

The compound of formula 2 was prepared using the method described in Example 25 for the preparation of the compound of formula 2 but using 5-bromo-2-ethylpyridine (1.86 g) in place of 6-iodo-2-picolin-5-ol. There was thus obtained 5-(4-bromophenyl)-2-ethylpyridine which was purified by flash column chromatography on silica gel using a gradient of 2% to 10% ethyl acetate in n-pentane as eluent to give an oil (1.2 g), NMR: 1.3(3H,t), 2.8(2H,q), 7.35(1H, d), 7.68(4H,s), 8.0(1H,d) and 8.8(1H,d), m/z 262 and 264 (M+H).

The 5-bromo-2-ethyl pyridine was prepared by the method of Tilley, J. W. et al, JOC, 53, (1988), 386–390.

EXAMPLE 29

$Ar^2$=1,2,4-oxadiazol-3-yl

Purified by flash column chromatography on silica gel using 10% methanol in dichloromethane containing 1% ammonia (density, 0.88 g/cm$^3$) as eluent, followed by recrysallisation from acetonitrile to give the title compound as a solid, m.p. 206°–207° C.; NMR: 1.21–1.45(1H,m), 1.48–1.70(1H,m), 1.75–2.03(3H,m), 2.56–2.8(4H,m), 2.80–2.92(1H,d), 3.08–3.15(1H,d), 5.67(1H,s), 7.61(2H,d), 8.04(2H,d) and 9.72(1H,s).

The compound of formula 2 (Z=iodo) used as starting material was prepared as follows.

A mixture of 4-iodobenzamidoxime (3.93 g) in triethylorthoformate (15 ml) was heated at reflux for 4 hours. The mixture was evaporated and the residue was purified by flash column chromatography on silica gel using 4:1 (v/v) n-pentane/ethyl acetate as eluent to give 3-(4-iodophenyl)-1,2,4-oxadiazole (0.74 g) as a solid; NMR(CDCl$_3$): 7.85 (4H,s) and 8.74(1H,s); m/z 272(M).

EXAMPLE 30

$Ar^2$=2-thiazolyl

Purified by flash column chromatography using a 4:1(v/v) mixture of dichloromethane/methanol as eluent to give a solid, m.p. 210°–212° C.; NMR: 1.2–1.4(1H,m), 1.5–1.7 (1H,m), 1.8–2.0(3H,m), 2.6–2.8(4H,m), 2.8–2.9(1H,d), 3.05–3.15(1H,d), 5.65(1H,s), 7.8(1H,d) and 7.93(1H,d).

The compound of formula 2, 4-bromophenyl-2-thiazole was prepared as described by Erlenmeyer, H., Helv. Chim. Acta., 33, (1950), 1271.

EXAMPLE 31

$Ar^2$=3-methyl-1,2,4-thiadiazol-5-yl

Purified by flash column chromatography using a 85:10:5 (v/v/v) mixture of ethyl acetate/methanol/ammonia to give the title compound as a solid, m.p. 186°–188° C.; NMR: 1.2–1.4(1H,m), 1.5–1.7(1H,m), 1.8–2.0(3H,m), 2.6–2.8(4H, m), 2.7–2.75(3H,s), 2.8–2.9(1H,d), 3.05–3.15(1H,d) and 5.65(1H,s).

The compound of formula 2, 3-methyl-5-(4-bromophenyl)-1,2,4-thiadiazole, used as starting material was prepared by the method described in J. Med. Chem., 33, (1990), 2052–2059.

EXAMPLE 32

2-ethyl-1,3,4-oxadiozol-5-yl

Purified by flash column chromatography on silica gel using 20% methanol in dichloromethane containing 1% ammonia (density, 0.88 g/cm$^3$) as eluent, followed by recrystallisation from acetonitrile, to give the title compound as a solid, m.p. 198°–199° C.; NMR: 1.25–1.45(1H,m), 1.33(3H,t), 1.50–1.70(1H,m), 1.78–2.03(3H,m), 2.65–2.8 (4H,m), 2.85–2.92(1H,d), 2.94(2H,q), 3.03–3.15(1H,d), 5.65(1H,s), 7.60(2H,d) and 7.96(2H,d).

The compound of formula 2 was prepared as follows.

A mixture of 4-bromobenzoic acid hydrazide (3.23 g) and triethylorthopropionate (25 ml) was heated at reflux for 7 hours. The mixture was evaporated to give a solid which was recrystallised from ethyl acetate to give 2-(4-bromphenyl)-5-ethyl-1,3,4-oxadiazole (3.65 g), as a solid, m.p. 101°–102° C.; microanalysis found: C, 47.3; H, 3.6; N, 10.9%; C$_{10}$H$_9$BrN$_2$O requires: C, 47.5; H, 3.58; N, 11.1%; NMR (CDCl$_3$): 1.44(3H,t), 2.96(2H,q), 7.65(2H,d) and 7.90(2h, D); m/z 253(M+H).

EXAMPLE 33

Using the procedure described in Example 1, but with 3-(4-iodophenyl)-5-methyl-1,2,4-oxadiazole in place of 3-(4-bromophenyl)pyridine and (+)-3-ethynyl-3-hydroxyquinuclidine in place of 3-ethynyl-3-hydroxyquinuclidine, there was thus obtained, after recrystallisation from ethanol, (+)-3-[2-(4-[5-methyl-1,2,4-oxadiazol-3-yl]phenyl)ethynyl]-3-hydroxy quinuclidine as a solid, m.p. 210°–211° C.; NMR: 1.25–1.45(1H,m), 1.55–1.75(1H,m), 1.85–2.03(3H,m), 2.65–2.8(4H,m), 2.7 (3H,s), 2.85–2.92(1H,d), 3.08–3.15(1H,d), 5.65(1H,s), 7.55–7.65(2H,d) and 7.93–8.03(2H,d); [α]$_D^{20}$=+29.0° (c=1.0, methanol); m/z 310(M+H).

The (+)-ethynyl-3-hydroxyquinuclidine was prepared as follows.

A solution of (±)-3-ethynyl-3-butyryloxyquinuclidine (4.42 g) in deionised water (700 ml) containing methanol (35 ml) was adjusted to pH 7.0 using an 0.1M aqueous sodium hydroxide solution (dispensed by a pH autotitrater). A suspension of pig liver eaterase (8.0 ml, 9200 units, in 3.2M aqueous ammonium sulphate solution at pH8; Sigma Chemical Company Ltd) was added to the reaction mixture and the mixture was stirred at ambient temperature whilst maintaining the pH at 7.0 using 0.1M aqueous sodium hydroxide solution (dispensed by a pH autotitrater). After 5.5 hours, 7.3 ml of the sodium hydroxide solution had been consumed, indicating that the hydrolysis was 35% complete. The pH of the reaction mixture was adjusted to 2.5 using 2M aqueous hydrochloric acid and the mixture was stirred for 10 minutes. 2M aqueous sodium hydroxide solution was then added to the mixture to give a pH of 7.05 and the mixture extracted with diethyl ether (3×200 ml, followed by 12×150 ml). The aqueous phase was separated, and freeze dried over a period of 48 hours to give a solid which was dissolved in deionised water (30 ml). The solution was filtered and the filtrate was basified to pH9 using 10.8M sodium hydroxide solution to give a solid. The solid was collected by filtration to give (+)-3-ethynyl-3-hydroxyquinuclidine, (554 mg) m.p. 204°–207° C., [α]$^{20}_D$=54.5° (C=0.99, methanol).

The (±)-3-ethynyl-3-butyryloxyquinuclidine used as starting material was prepared as follows.

A solution of n-butyl lithium (100 ml of a 2M solution in pentane) was added portion-wise over a period of 20 minutes to a stirred solution of ethynyltrimethylsilane (19.6 g) in dry tetrahydrofuran (400 ml) at −70° C. The mixture was stirred for 1 hour at −70° C. A solution of 3-quinuclidinone (2.4 g) in dry tetrahydrofuran (100 ml) was then added and the mixture stirred for 1 hour at −70° C. Methanol (1 ml) was then added to the mixture and the mixture allowed to warm to ambient temperature. The solvents were removed by evaporation. Methanol (500 ml) and potassium carbonate (40 g) were added to the residue and the mixture was stirred for 1 hour. The solvent was removed by evaporation. The residue was triturated with water (500 ml) and then dried in vacuo to give 3-ethynyl-3-hydroxy-quinuclidine as a solid, m.p. 193°–197° C.; NMR(DMSO-d$_6$): 1.5–1.3(1H,m), 1.4–1.6(1H,m), 1.7–1.95(3H,m), 2.55–2.8(5H,m), 2.95(1H, d), 3.3(1H,d) and 5.4(1H,s); m/z 152 (M+H).

A mixture of (±)-3-ethynyl-3-hydroxyquinuclidine (15.1 g) and butyric anhydride (60 ml) was stirred at 120° C. for 5 hours. The reaction mixture was cooled to ambient temperature, added to a saturated aqueous solution of sodium carbonate (1 l) and stirred for 3 hours. The mixture was extracted with diethyl ether (3×100 ml). The diethyl ether extracts were combined, washed with saturated aqueous sodium carbonate solution, dried (MgSO$_4$) and evaporated to give (±)-3-ethynyl-3-butyryloxyquinuclidine as an oil, NMR(200 MHz, DMSOd$_6$): 0.90(3H,t), 1.40(1H,m), 1.57(4H,m), 1.85(1H,m), 2.28(3H,m), 2.66(4H,m), 3.03 (1H,d), 3.18(1H,d) and 3.55(1H,s).

EXAMPLE 34

The procedure described in Example 33 was repeated using (−)-3-ethynyl-3-hydroxyquinuclidine in place of (+)-3-ethynyl-3-hydroxyquinuclidine to give (−)-3-[2-(4-[5-methyl-1,2,4-oxadiazol-3-yl]phenyl)ethynyl]-3-hydroxy quinuclidine as a solid, m.p. 211°–212° C.; NMR: 1.25–1.45 (1H,m), 1.55–1.75(1H,m), 1.85–2.03(3H,m), 2.65–2.8(4H, m), 2.7(3H,s), 2.85–2.92(1H,d), 3.08–3.15(1H,d), 5.65(1H, s), 7.5–7.7(2H,d) and 7.93–8.03(2H,d); [α]$_D^{20}$=−31.2° (c=1, methanol); m/z 310(M+H).

The (−)-3-ethynyl-3-hydroxyquinuclidine was prepared as follows.

A solution of (±)-3-ethynyl-3-butyryloxy quinuclidine (4.42 g) in deionised water (700 ml) containing methanol (35 ml) was adjusted to pH 7.0 using 0.1M aqueous sodium hydroxide solution (dispensed by a pH autotitrator). A suspension of pig liver esterase (3.0 ml, 3450 units, in 3.2M aqueous ammonium sulphate solution at pH8; Sigma Chemical Company Ltd) was added to the reaction mixture and the mixture stirred at ambient temperature for 46 hours whilst maintaining the pH at 7.0 using 0.1M aqueous sodium hyroxide solution (dispensed from a pH autotitrater). During this period 112.5 ml of the sodium hydroxide solution was consumed, indicating that the hydrolysis was 56% complete. The pH of the reaction mixture was adjusted to 2.52 using 2M aqueous hydrochloric acid and the mixture stirred for 20 minutes. 2M aqueous sodium hydroxide solution was added to the mixture to give a pH of 7.01 and the mixture extracted with diethyl ether (12×150 ml). The diethyl ether extracts were combined, dried (MgSO$_4$) and evaporated to give an oil (2.43 g) containing (−)-3-ethynyl-3-butyryloxyquinuclidine and some butyric acid.

The above oil containing (−)-3-ethynyl-3-butyryloxyquinuclidine was treated with a solution of potassium hydroxide (2.24 g) in methanol (50 ml). The mixture was stirred at ambient temperature for 2 hours. The mixture was evaporated and deionised water (2 ml) was added to the residue to give a solid. The solid was collected by filtration, washed with water (2×2 ml) and dried under vacuum over phosporus pentoxide to give (−)-3-ethynyl-3-hydroxyquinuclidine (611 mg) as a solid, m.p. 199°–202° C., [α]$^{19}_D$=−56.1° (C=1.02, methanol).

EXAMPLE 35

Using a procedure similar to that described in Example 1, but using 3-(3-bromophenyl)-5-methyl-1,2,4-oxadiazole in place of 3-(4-bromophenyl)pyridine, there was obtained (after purification by flash column chromatography on silica gel using 10% methanol in dichloromethane containing 1% ammonia, as eluent, followed by recrystallisation from acetonitrile) 3-[2-(3-[5-methyl-1,2,4-oxadiazol-3-yl] phenyl)ethynyl]-3-hydroxyquinuclidine as a solid, m.p. 182°–183° C.; NMR: 1.25–1.45(1H,m), 1.50–1.75(1H,m), 1.78–2.03(3H,m), 2.55–2.8(4H,m), 2.67(3H,s), 2.78–2.92 (1H,d), 3.05–3.15(1H,d), 5.65(1H,s), 7.50–7.65(2H,m) and 7.9–8.01(2H,m).

The compound of formula 2, 3-(3-bromophenyl)-5-methyl-1,2,4-oxadiazole was prepared from 3-bromobenzonitrile using the method described in Example 8 for the preparation of 3-(4-iodophenyl)-5-methyl-1,2,4-oxadiazole. There was thus obtained 3-(3-bromophenyl)-5-methyl-1,2,4-oxadiazole as a solid, m.p. 78°–79° C.; microanalysis, found: C, 44.9; H, 2.8; N, 11.5%; $C_9H_7BrN_2O$ requires: C, 45.2; H, 2.95; N, 11.7%; NNR: 2.67(3H,s), 7.51–7.58(1H,m), 7.80(1H,dd), 8.00(1H,dd) and 8.11(1H,d); m/z 239 (M+H).

EXAMPLE 36

Using a procedure similar to that described in Example 1, but using 3-methyl-5-(3-bromophenyl)-1,2,4-oxadiazole in place of 3-(4-bromophenyl)pyridine, there was obtained [after purification by flash column chromatography on silica gel using 10% methanol in dichloromethane containing 1% ammonia (density, 0.88 g/cm$^3$) as eluent] 3-[2-(3-[3-methyl-1,2,4-oxadiazol-5-yl]phenyl)ethnynyl]-3-hydroxy quinuclidine as a solid, m.p. 178°–180° C.; NMR: 1.25–1.45(1H,m), 1.52–1.73(1H,m), 1.80–2.06(3H,m), 2.45(3H,s), 2.65–2.8 (4H,m), 2.82–2.95(1H,d), 3.08–3.22(1H,d), 5.70(1H,s), 7.60–7.78(2H,m) and 8.04–8.13(2H,m).

The starting material, 3-methyl-5-(3-bromophenyl)-1,2,4-oxadiazole, was prepared from ethyl-3-bromobenzoate using the method described in Example 11 for the preparation of 3-methyl-5-(4-iodophenyl)-1,2,4-oxadiazole. There was thus obtained 3-methyl-5-(3-bromophenyl)-1,2,4-oxadiazole as a solid, m.p. 90°–92° C.; microanalysis, found: C, 45.4; H, 2.9; N, 11.3%; $C_9H_7BrN_2O$ requires: C, 45.2; H, 2.95; N, 11.7%; NMR: 2.43(3H,s), 7.59(1H,t), 7.91(1H,dd), 8.10(1H,dd), 8.20(1H,d); m/z 239 (M+H).

EXAMPLE 37

The procedure described in Example 1 was repeated but using 3-methyl-5-(3-allyl-4-trifluoromethylsulphonyloxyphenyl-1,2,4-oxadiazole in place of 3-(4-bromophenyl)pyridine. There was thus obtained, after recrystallisation from acetonitrile, 3-[2-(2-allyl-4-(3-methyl-1,2,4-oxazdiazol-5-yl)phenylethynyl]-3-hydroxyquinuclidine as a solid, m.p. 164°–165° C.; NMR: 1.25–1.45(1H,m), 1.52–1.72(1H,m), 1.8–2.05(3H,m), 2.41 (3H,s), 2.67–2.8(4H,m), 2.8–2.45(1H,d), 3.1–3.25(1H,d), 3.61(2H,d), 5.06–5.20(2H,d), 5.70(1H,s), 5.42–6.10(1H,m), 7.61(1H,d) and 7.89–8.00(2H,m).

The 3-methyl-5-(3-allyl-4-trifluoromethylsulphonyloxyphenyl)-1,2,4-oxadiazole was prepared by treating 3-methyl-5-(3-allyl-4-hydroxyphenyl)-1,2,4-oxadiazole with triflic anhydride in pyridine at 0° C. using the procedure described in Example 43 to give an oil which was used without further purification.

EXAMPLE 38

A solution of hydrogen chloride in ethanol was added dropwise to a stirred solution of 3-[2-allyl-4-(3-methyl-1,2, 4-oxadiazol-5-yl)phenoxymethyl]-3-hydroxyquinuclidine borane complex (0.7 g) in acetone (7 ml) until the solution was pH1. The solution was stirred at ambient temperature for 1 hour. The mixture was diluted with ether (5 ml) and stirred for 30 minutes. The solid was collected by filtration and washed with ether to give 3-[2-allyl-4-(3-methyl-1,2,4-oxadiazol-5-yl)phenoxymethyl]-3-hydroxy quinuclidine hydrochloride as a colourless solid (0.56 g), m.p. 157°–160° C.; microanalysis, found: C, 61.2; H, 6.8; N, 10.6%; $C_{20}H_{25}N_3O_3$. HCl requires: C, 61.3; H, 6.7; N, 10.7%; NMR: 1.6–2.0(3H,m), 2.1–2.5(2H,m), 2.3–2.4(3H,s), 3.0–3.45(6H,m), 3.4–3.55(2H,d), 4.1–4.3(2H,q), 5.0–5.2 (2H,m), 5.3–5.8(1H,br), 5.9–6.1(1H,m), 7.15–7.25(1H,d), 7.8–7.9(1H,s), 7.9–8.0(1H,d), 10.6–10.9(1H,s); m/z 356 (M+H).

The 3-[2-allyl-4-(3-methyl-1,2,4-oxadiazol-5-yl) phenoxymethyl]-3-hydroxyquinuclidine borane complex used as starting material was prepared as follows.

A mixture of ethyl 4-hydroxy benzoate (154 g), anhydrous potassium carbonate (141 g), allyl bromide (80 ml) and acetone (350 ml) was heated at reflux for 17 hours. The reaction mixture was cooled to ambient temperature, filtered and the filtrate was evaporated. The residue was dissolved in diethyl ether (1 l) and the solution was washed successively with aqueus 2M aqueous sodium hydroxide solution (3×100 ml), water (3×250 ml), dried (Na$_2$SO$_4$) and evaporated to give ethyl 4-allyloxybenzoate as an oil (171 g), NMR (CDCl$_3$): 1.3–1.4(3H,t), 4.3–4.4(2H,q), 4.55–4.65(2H,m), 5.25–5.5(2H,m), 5.95–6.15(1H,m), 6.9–7.0(2H,d) and 7.95–8.05(2H,d).

Acetamide oxime hydrochloride (10.9 g) was added portionwise to a stirred, ice-cooled, suspension of sodium hydride (60% w/w dispersion in mineral oil, 7.9 g; the oil was removed by washing the solid with petroleum ether) in dry tetrahydrofuran (250 ml) under an atmosphere of argon, whilst maintaining the temperature at 5° C. The mixture was stirred at 5° to 10° C. for 40 minutes.

Freshly ground 4A molecular sieve (40 g) and a solution of ethyl 4-allyloxybenzoate (15.6 g) in dry tetrahydrofuran (50 ml) was then added to the mixture. The mixture was stirred for 2 days at ambient temperature. The mixture was filtered through diatomaceous earth and the filtercake was extracted with ethyl acetate (3×100 ml). The tetrahydrofuran filtrate and ethyl acetate washings were combined and evaporated. The residue was dissolved in ethyl acetate (250 ml). The solution was washed with water (2×100 ml), dried (Na$_2$SO$_4$) and evaporated. The residue was triturated with pentane to give a solid (6.6 g) which was purified by column chromatography on silica gel (Merck 7736) using dichloromethane as eluent, to give, after recrystallisation from cyclohexane, 5-(4-allyloxyphenyl)-3-methyl-1,2,4-oxadiazole as a solid (4.9 g), m.p. 52°–54° C.; microanalysis, found: C, 66.8; H, 5.6; N, 12.9%; $C_{12}H_{12}N_2O_2$ requires: C, 66.7; H, 5.6; N, 13.0%; NMR (CDCl$_3$): 2.4–2.5(3H,s), 4.6–4.65(2H,m), 5.3–5.5(2H,q), 5.95–6.05(1H,m), 6.95–7.05(2H,d) and 8.0–8.1(2H,d); m/z 217(M+H).

5-(4-allyloxyphenyl)-3-methyl-1,2,4-oxadiazole (1.2 g) and diphenyl ether (5 ml) were warmed gently to give a solution. This stirred solution, under an atmosphere of argon, was immersed in an oil bath at 265° C. for 12 minutes. This procedure was repeated three times. The deep red solutions were combined, diluted with diethyl ether (100 ml) and extracted with aqueous 1M sodium hydroxide (3×20 ml). The alkaline extracts were combined, washed with ether (3×30 ml), cooled in ice-water, acidified with aqueous 5M hydrochloric acid (15 ml), and extracted with ether (3×60 ml). The ether extracts were combined, washed with saturated brine (25 ml), dried ($Na_2SO_4$) and evaporated. The residue was purified by flash column chromatography on silica gel using 20% ethyl acetate/n-pentane as eluent, to give 2-allyl-4-(3-methyl-1,2,4-oxadiazol-5-yl)phenol as a solid m.p. 135°–137° C.; microanalysis, found: C, 66.7; H, 5.8; N, 12.5%; $C_{12}H_{12}N_2O_2$ requires: C, 66.7; H, 5.6; N, 13.0%; NMR: 2.3–2.35(3H,s), 3.3–3.4(2H,d), 5.0–5.15(2H, m), 5.85–6.1(1H,m), 6.95–7.05(1H,d), 7.75–7.8(2H,m) and 10.4–10.5(1H,s); m/z 217 (M+H).

A mixture of 2-allyl-4-(3-methyl-1,2,4-oxadiazol-5-yl) phenol (0.7 g), 3-methylenequinuclidine oxide borane complex (0.5 g) and powdered potassium carbonate (0.9 g) in dry dimethylformamide (10 ml) was stirred at 70° C. for 4 hours. The mixture was poured into water (100 ml) and extracted with ethyl acetate (3×70 ml). The ethyl acetate extracts were combined, washed with water (4×30 ml), dried ($Na_2SO_4$) and evaporated. The residue was purified by flash column chromatography on silica gel using successively dichloromethane, pentane and 50% diethyl ether/pentane as eluent to remove impurities; then using diethyl ether as eluent to give 3-[2-allyl-4-(3-methyl-1,2,4-oxadiazol-5-yl)phenoxymethyl]-3-hydroxy quinuclidine borane complex as a solid (0.8 g), m.p. 133°–135° C.; NMR($CDCl_3$): 0.6–2.5 (3H,br), 1.6–1.75(1H,m), 1.7–1.9(2H,m), 2.2–2.4(2H,m), 2.45(3H,s), 2.7(1H,s), 2.7–3.3(6H,m), 3.4–3.5(2Hd), 3.95–4.15(2H,q), 4.95–5.2(2H,m), 5.85–6.1(1H,m), 6.9–7.0 (1H,d), 7.9–7.95(1H,s) and 7.95–8.05(1H,d).

EXAMPLE 39

The procedure described in Example 38 was repeated using 3-[2-allyl-4-(5-methyl-1,2,4-oxadiazol-3-yl) phenoxymethyl]-3-hydroxyquinuclidine borane complex (0.85 g) instead of 3-[2-allyl-4-(3-methyl-1,2,4-oxadiazol-5-yl)phenoxymethyl]-3-hydroxyquinuclidine borane complex. There was thus obtained, after recrystallisation from isopropanol, 3-[2-allyl-4-(5-methyl-1,2,4-oxadiazol-3-yl) phenoxymethyl]-3-hydroxyquinuclidine hydrochloride as a solid (0.60 g), m.p. 133°–135° C.; NMR: 1.55–2.05(3H,m), 2.1–2.4(2H,m), 2.6–2.7(3H,s), 3.0–3.4(6H,m), 3.4–3.5(2H, d), 4.05–4.3(2H,q), 5.0–5.2(2H,m), 5.5–5.65(1H,s), 5.9–6.1 (1H,m), 7.1–7.2(1H,d), 7.7–7.8(1H,s), 7.8–7.9(1H,d); m/z 356(M+H).

The 3-[2-allyl-4-(5-methyl-1,2,4-oxadiazol-3-yl) phenoxymethyl]-3-hydroxyquinuclidine borane complex used as starting material was prepared as follows.

A solution of 2-allyl-4-cyanophenol (5.5 g), hydroxylamine hydrochloride (8.5 g) and sodium carbonate (6.1 g) in aqueous ethanol was heated at reflux for 3 hours. The solution was cooled to ambient temperature and the ethanol was removed by evaporation. The solid was collected by filtration, dissolved in ethanol and the solution was filtered. The filtrate was evaporated and the residual solid was triturated with hexane to give 3-allyl-4-hydroxybenzamidoxime as a solid (5.5 g), m.p. 144° C.

The 2-allyl-4-cyanophenol was prepared as follows.

A solution of 4-cyanophenol (50 g), allyl bromide (27.2 ml) potassium carbonate (47.8 g) in acetone (100 ml) was heated at reflux for 16 hours. The reaction mixture was evaporated, water was added to the residue and the aqueous mixture was extracted with diethyl ether. The diethyl ether extract was washed with dilute aqueous sodium hydroxide solution, dried ($MgSO_4$) and evaporated to give 4-cyanophenyl allyl ether as a solid, m.p. 41.6° C.; microanalysis, found: C 75.1; H, 5.8; N, 8.7%; $C_{10}H_9NO_2$ requires: C, 75.5; H, 5.7; N, 8.8%; NMR: 4.55–4.65(2H,m), 5.2–5.4(2H,m), 5.9–6.05(1H,m), 7.0–7.1(2H,m) and 7.65–7.75(2H,m).

A solution of allyl 4-cyanophenyl ether (12 g) in diphenylether (20 ml) was heated at 260° C. for 30 minutes. The reaction mixture was cooled to ambient temperature, diethyl ether was added and the mixture was extracted with 1M aqueous sodium hydroxide solution. The aqueous phase was separated, acidified with 2M aqueous hydrochloric acid solution and extracted with diethyl ether. The organic phase was separated, dried ($MgSO_4$) and evaporated to give 2-allyl-4-cyanophenol as a solid (11.4 g), m.p. 70° C.; microanalysis, found: C, 73.7; H, 5.6; N, 9.2%; $C_{10}H_9NO$. $0.25H_2O$ requires: C, 73.4; H, 5.8; N, 8.6%; NMR: 3.2–3.5 (2H,d), 5.0–5.1(2H,m), 5.85–6.05(1H,m), 6.9–7.0(1H,d), 7.4–7.5(2H,m) and 10.6(1H,s).

Acetyl chloride (2.28 ml) was added dropwise to a solution of 3-allyl-4-hydroxybenzamidoxime (5.4 g) in pyridine (48 ml). The solution was heated at reflux for 16 hours, cooled to ambient temperature and evaporated. The residue was dissolved in ethyl acetate and the solution was washed with saturated aqueous sodium carbonate solution, dried ($MgSO_4$) and evaporated, to give 2-allyl-4-(5-methyl-1,2,4-oxadiazol-3-yl)phenol as a low-melting solid (3.8 g), m/z 217 (M+H).

The procedure described in Example 38 was repeated using 2-allyl-4-(5-methyl-1,2,4-oxadiazol-3-yl)phenol instead of 2-allyl-4-(3-methyl-1,2,4-oxadiazol-5-yl)phenol. There was thus obtained, after flash column chromatography on silica gel using a gradient of 0 to 2% ethyl acetate/dichloromethane as eluent, 3-[2-allyl-4-(5-methyl-1,2,4-oxadiazol-3-yl)phenoxymethyl]-3-hydroxyquinuclidine borane complex as a colourless solid, m.p. 132°–135° C. eff; NMR($CDCl_3$): 0.7–2.3(3H,br), 1.6–1.75(1H,m), 1.75–1.9 (2H,m), 2.2–2.4(2H,m), 2.6–2.7(3H,s), 2.7–2.8(1H,s), 2.8–3.3(6H,m), 3.4–3.5(2H,d), 3.95–4.15(2H,q), 4.95–5.15 (2H,m), 5.9–6.1(1H,m), 6.85–6.95(1H,d), 7.85–7.9(1H,s) and 7.9–8.0(1H,d).

EXAMPLE 40

The procedure described in Example 38 was repeated using (E)-3-[4-(3-methyl-1,2,4-oxadiazol-5-yl)-2-propenylphenoxymethyl]-3-hydroxyquinuclidine borane complex instead of 3-[2-allyl-4-(3-methyl-1,2,4-oxadiazol-5-yl)phenoxymethyl]-3-hydroxy quinuclidine borane complex. There was thus obtained (E)-3-[4-(3-methyl-1,2,4-oxadiazol-5-yl)-2-propenylphenoxymethyl]-3-hydroxyquinuclidine hydrochloride as a solid, m.p. 160°–162° C.; microanalysis, found: C, 59.8; H, 6.9; N, 10.3%; $C_{20}H_{25}N_3O_3$. HCl. 0.5 $H_2O$ requires: C, 59.9; H, 6.8; N, 10.5%; NMR: 1.6–1.8(1H,m), 1.8–2.05(5H,m), 2.15–2.35(2H,m), 2.35–2.5(3H,s), 3.0–3.4(6H,m), 4.1–4.3 (2H,q), 5.6–5.65(1H,s), 6.35–6.55(1H,m), 6.7–6.85(1H,d), 7.2–7.3(1H,d), 7.9–8.0(1H,d), 8.05–8.1(1H,s)1 m/z 356 (M+H).

The (E)-3-[4-(3-methyl-1,2,4-oxadiazol-5-yl)-2-propenylphenoxymethyl]-3-hydroxyquinuclidine borane complex used as starting material was prepared as follows.

Acetamide oxime hydrochloride (0.44 g) was added in one portion to a stirred suspension of sodium hydride (60% w/w dispersion in mineral oil, 0.32 g; the oil was removed by washing the solid with petroleum ether) in dry tetrahydrofuran (20 ml) under an atmosphere of argon. The mixture was stirred at ambient temperature for 30 minutes.

4A molecular sieve (3.2 g) and a solution of (E)-3-(4-ethoxycarbonyl-2-propenylphenoxymethyl)-3- hydroxyquinuclidine borane complex (1.44 g) in dry tetrahydrofuran (20 ml) was then added to the mixture. The mixture was stirred for 4 hours at 60° C. The mixture was poured into water (70 ml) and the mixture was extracted with ethyl acetate (3×70 ml). The ethyl acetate extracts were combined, washed with water (3×25 ml), dried (NaSO₄) and evaporated. The residue was purified by flash column chromatography on silica gel using 25% ethyl acetate/n-pentane as eluent to give (E)-3-[4-(3-methyl-1,2,4-oxadiazol-5-yl)-2-propenylphenoxymethyl]-3-hydroxyquinuclidine borane complex as a solid (0.55 g), m.p. 160°–163° C.; NMR (CDCl₃): 0.7–2.2(3H,br), 1.5–1.9(3H,m), 1.9–2.05(3H,d), 2.2–2.5(2H,m), 2.4–2.5(3H,s), 2.6–2.65(1H,s), 2.8–3.3(6H, m), 4.0–4.15(2H,q), 6.3–6.45(1H,m), 6.55–6.65(1H,d), 6.9–7.0(1H,d), 7.9–8.0(1H,d) and 8.15–8.2(1H,s).

EXAMPLE 41

A mixture of 3-(2-tri-n-butylethenylstannane)-3-hydroxyquinuclidine (E/Z, 85:15) (0.88 g), 3-iodo-5-ethyl-1,2,4-oxadiazole (0.93 g), tris(dibenzylidine acetone) dipalladium (0) (0.1 g) and cuprous iodide (0.1 g) and anhydrous dimethyl formamide (6 ml) was stirred under an atmosphere of argon. The reaction mixture was heated at 90° C. for 2 hours. The reaction mixture was cooled to ambient temperature, diluted with methylene chloride (150 ml) and washed with 10% aqueous sodium carbonate solution (4×25 ml). The organic extracts were combined, dried (MgSO₄), and evaporated. The residue was purified by column chromatography on silica gel using a 90:10:0.5 (v/v/v) mixture of methylene chloride, methanol and ammonia as eluent to give a residue which was triturated with ethyl acetate to give 3-[2-(E)-(4-[5-ethyl-1,2,4-oxadiazol-3-yl]phenyl)ethenyl]-3-hydroxy quinuclidine as a solid, m.p. 158°–160° C.; NMR: 1.13–1.60(5H,m), 1.70(2H,br), 1.98(1H,m), 2.55–3.10(8H,m), 4.62(1H,s), 6.63–6.83(2H,q), 7.60–7.96 (4H,q)

The 3-(2-tri-n-butylethenyl stannane)-3-hydroxyquinuclidine used as starting material was obtained as follows.

A mixture of 3-ethynyl-3-hydroxyquinuclidine (0.75 g), tri-n-butyl tin hydride (1.48 ml) and of αα'-azo-isobutyronitrile (0.02 g) was heated at 100° C. for 10 minutes. The residue was purified by column chromatography on silica-gel using a 90:10:0.5 (v/v/v) mixture of dichloromethane, methanol and ammonia as eluent to give 3-(2-tri-n-butylethenyl stannane)-3-hydroxyquinuclidine as a solid, m.p. 62°–3° C.; microanalysis, found: C, 56.0; H, 9.7; N, 3.0%; C₂₁H₄₁NOSn 0.5 CH₃OH requires: C, 56.4; H, 9.3 N 3.1%; NMR: 0.88(9H,m), 0.8–2.0(23H,m), 2.5–2.9 (6H,m), 4.04(1H,s) and 6.12(2H,m); m/z 444(M+H).

EXAMPLE 42

The procedure described in Example 41 was repeated but using 3-iodo-5-isopropyl-1,2,4-oxadiazole in place of 3-iodo-5-methyl-1,2,4-oxadiazole to give 3-[2-(E)-(4-[5-isopropyl-1,2,4-oxadiazol-3-yl]phenyl)ethenyl]-3-hydroxy quinuclidine as a solid, m.p. 142°–144° C.; NMR: 1.1–1.58 (8H,m), 1.7(2H,br), 1.9–2.1(1H,br), 2.6–2.93(6H,m), 3.25–3.46(1H,m), 4.8(1H,s), 6.63–6.83(2H,q) and 7.6–7.96 (4H,q).

EXAMPLE 43

The procedure described in Example 1 was repeated but using 5-methyl-3-(3-allyl-4-trifluoromethylsulphonyloxyphenyl)-1,2,4-oxadiazole in place of 3-(4-bromophenyl)pyridine. There was thus obtained, after purification by flash column chromatography on silica gel using 10% methanol in dichloromethane containing 1% ammonia followed by recrystallisation from acetonitrile, 3-[2-(2-allyl-4-(5-methyl-1,2,4-oxadiazol-5-yl) ethynyl]-3-hydroxyquinuclidine as a solid, m.p. 135°–137° C., NMR: 1.2–2.0(5H,m), 2.55(3H,s), 3.0(2H,m), 3.6(2H,d), 5.1(1H,br.s), 5.15(1H,m), 5.7(1H,m), 5.9–6.1(1H,m), 7.55 (1H,d) and 7.85(2H,m).

The 5-methyl-3-(3-allyl-4-trifluoromethylsulphonyloxyphenyl)-1,2,4-oxadiazole was prepared as follows.

Triflic anhydride (1.4 ml) was added dropwise to a stirred solution of 5-methyl-3-(3-allyl-4-hydroxyphenyl)1,2,4-oxadiazole (1.2 g) in pyridine (10 ml) cooled in an ice-bath. The mixture was stirred for 45 minutes. The mixture was diluted with 1M aqueous hydrochloric acid (200 ml) and extracted with ethyl acetate (200 ml). The organic extract was washed with 1M aqueous hydrochloric acid, aqueous sodium bicarbonate solution, and brine, then dried (MgSO₄), and evaporated to give 5-methyl-3-(3-allyl-4-trifluoromethylsulphonyloxyphenyl)-1,2,4-oxadiazole (1.37 g) as a solid, NMR: 8.1(2H,m), 7.6(1H,d), 6.1–5.9(1H,m), 5.3–5.1(2H,m), 3.55(2H,d) and 2.7(3H,s); m/z 351 (M+H).

EXAMPLE 44

The procedure described in Example 4 was repeated using 3-(4-iodophenyl)-5-methyl-1,2,4-oxadiazole in place of 3-(4-bromophenyl)pyridine to give 3-[2-(4-(5-methyl-1,2,4-oxadiazol-3-yl)phenyl)ethenyl]-3-hydroxyquinuclidine which was purified by flash column chromatography on silica gel using a gradient of 10% to 20% methanol in dichloromethane containing 1% ammonia (density, 0.88 g/cm³) followed by recrystallisation from acetone to give a solid with m.p. 188°–189° C.; NMR: 1.28(1H,m), 1.5(1H, m), 1.72(2H,m), 2.02(1H,m), 2.7(8H,m), 2.9(1H,d), 4.8(1H, s), 6.67(1H,d), 6.8(1H,d), 7.63(2H,d) and 7.95(2H,d).

EXAMPLE 45

A mixture of 3-[2-(4-(5-methyl-1,2,4-oxadiazole-3-yl) phenyl)ethynyl]-3-hydroxyquinuclidine (0.61 g) and 5% Pd on carbon (60 mg) in ethanol (100 ml) was hydrogenated at atmospheric pressure for 4 hours. The mixture was filtered and the filtrate was evaporated. The residue was purified by flash chromatography on silica gel eluting with 10% methanol in dichloromethane containing 1% ammonia (density, 0.88 g/cm³), to give 3-[2-(4-(5-methyl-1,2,4-oxadiazol-3-yl) phenyl)ethyl]-3-hydroxyquinuclidine (0.15 g) as a solid, m.p. 165°–167° C.; NMR: 1.2–2.1(7H,m), 2.9–2.65(8H,m), 2.65(3H,s), 4.5(1H,s), 7.4(2H,d) and 7.9(2H,d); m/z 314 (M+H).

EXAMPLE 46

A solution of 3-aminoquinuclidine (187 mg) and 4-(3-pyridyl)benzaldehyde (272 mg) in toluene (50 ml) was heated at reflux for 4 hours using a Dean and Stark water separator. The toluene was evaporated and the residue dissolved in methanol (30 ml). Sodium borohydride (112 mg) was added and the mixture stirred for 2 hours. The methanol was evaporated and 1M aqueous hydrochloric acid (10 ml) added and made basic by adding sodium hydroxide solution (1.35 g/cm³). The mixture was extracted with diethyl ether (3×20 ml) and the combined extracts dried (Na₂SO₄) and evaporated. The residue was treated with excess of ethereal hydrogen chloride solution and the precipitate crystallised from methanol/ethyl acetate to give 3-[4-(3-pyridyl)phenylmethylamino]quinuclidine hydrochloride as a colourless solid (405 mg), m.p. 266°–268° C.; microanalysis, found: C 56.2; H, 6.6; N, 10.0%; C₁₉H₂₃N₃. 3HCl requires: C, 56.6; H, 6.5 N, 10.4%; NMR(DMSO-d₆/CD₃CO₂D): 1.68–2.10(3H,m), 2.65(1H,m), 3.12–3.38(3H, m), 3.44–3.65(2H,m), 3.70(3H,t), 3.68–3.90(1H,m), 4.38

(2H,s), 7.84–8.00(4H,m), 8.00–8.10(1H,m), 8.78(1H,d), 8.86(1H,d) and 9.20(1H,s).

The starting aldehyde was obtained as follows: Diethyl 3-pyridylborane (1.51 g), powdered potassium hydroxide (1.71 g) and teteramethylammonium bromide (330 mg) were added to a solution of tetrakistriphenylphosphine palladium [0] (528 mg) and 4-bromobenzaldehyde dimethyl acetal (3.55 g) in anhydrous tetrahydrofuran (60 ml). The mixture was heated at reflux for 2 hours, the THF evaporated and the residue dissolved in ether (200 ml). The ether solution was washed with saturated brine (2×100 ml), dried ($Na_2SO_4$) and evaporated to an oil. The oil was purified by column chromatography on alumina, eluting with 10% ethyl acetate in hexane to give 4-(3-pyridyl)benzaldehyde dimethyl acetal (1.72 g). NMR($CDCl_3$): 3.37(6H,s), 5.45(1H,s), 7.45(1H,m), 7.58(4H,m), 7.89(1H,m), 8.59(1H,dd) and 8.85 (1H,d). This diacetal (5.0 g) was stirred in 1M aqueous hydrochloric acid (30 ml) for 45 minutes and the mixture neutralised with 1M aqueous sodium hydroxide solution (30 ml) and extracted with ether (3×60 ml). The ether extracts were combined, washed with saturated brine, dried ($Na_2SO_4$) and evaporated to give 4-(3-pyridyl)benzaldehyde (3.41 g) as an oil which gave a solid on standing. m.p 48°–51° C.; NMR($CDCl_3$): 7.43(1H,q), 7.76(2H,m), 7.92 (1H,m), 8.01(2H,m), 8.65(1H,dd), 8.90(1H,d) and 10.09 (1H,s).

EXAMPLE 47

A mixture of 3-(4-iodophenyl)-5-methyl-1,2,4-oxadiazole (1.43 g), 3-vinylquinuclidine (685 mg), bis (triphenylphosphine)palladium (II) chloride (175 mg), copper (I) iodide (90 mg) and triethylamine (5.0 ml) in dry dimethylformamide (10 ml) was stirred under argon at 100° C. for 5 hours. The dimethylformamide and triethylamine were removed by evaporation. The residue was treated with 2M aqueous sodium hydroxide solution (20 ml) and extracted with dichloromethane (3×20 ml). The organic extracts were washed with water (20 ml), dried ($MgSO_4$) and evaporated. The residue was purified by flash column chromatography on silica gel using 5% methanol in dichloromethane containing 0.5% ammonia (density, 0.88 g/cm$^3$) as eluent to give E-3-[2-{4-(5-methyl-1,2,4-oxadiazol-3-yl) phenyl}ethenyl]quinuclidine (150 mg) as a solid, m.p. 93°–97° C.; NMR: 1.4(1H,m), 1.65(2H,m), 1.8(2H,m), 2.55 (1H,m), 2.65(3H,s), 2.8(4H,m), 3.08(1H,m), 3.45(1H,m), 6.5(1H,d), 6.62(1H,d,d), 7.6(2H,d) and 7.82(2H,d).

EXAMPLE 48

A mixture of 3-ethynyl-3-hydroxyquinuclidine (1.06 g), 2-(4-bromopbenyl)-1,3,4-oxadiazole (1.58 g), bis (triphenylphosphine)palladium (II) chloride (245 mg), copper (I) iodide (123 mg), triethylamine (7 ml) and dimethylformamide (14 ml) were heated at 65° C. under an atmosphere of argon for 4 hours. The triethylamine and DHF were removed by evaporation. An aqueous solution of sodium hydroxide (2M, 20 ml) was added to the residue and the mixture extracted with dichloromethane (3×30 ml). The organic extracts were combined, dried ($MgSO_4$) and evaporated. The residue was purified by flash column chromatography on silica gel eluting with 10% methanol in dichloromethane containing 1% ammonia (density 0.88 g/cm$^3$) to give 3-[2-(4-[1,3,4-oxadiazol-2-yl]phenyl)ethynyl]-3-hydroxyquinuclidine (811 mg) as a solid, m.p. 229–230%; microanalysis, found: C, 67.9; H, 5.8; N, 14.2%; $C_{17}H_{17}N_3O_3$, 0.4 $H_2O$ requires: C, 67.5; H, 5.9; N, 13.9; NMR: 1.20–1.44(1H,m), 1.50–1.71(1H,m), 1.77–2.04(3H, m), 2.69(4H,t), 2.79–2.94(1H,d), 3.04–3.20(1H,d), 5.69(1H, s), 7.63(2H,d), 8.03(2H,d), 9.35(1H,s); m/z 296(M+H).

The 2-(4-bromophenyl)-1,3,4-oxadiazole used as starting material was obtained as follows:

A mixture of 4-bromobenzoylhydrazine (3.23 g) and triethylorthoformate (25 ml) was heated at reflux for 30 hours. The mixture was evaported to give a solid (1.69 g) which was used without further purification; NMR: 7.68 (2H,d), 7.95(2H,d), 8.48(1H,s); m/z 225(M+H).

EXAMPLE 49

A mixture of 3-ethynyl-3-hydroxyquinuclidine (0.3 g), 2-methyl-5-(4-bromophenyl)tetrazole (0.48 g), bis (triphenylphosphine)-palladium (II) chloride (70 mg), copper (I) iodide (35 mg), triethylamine (1 ml) and dimethylformamide (2 ml) was stirred at 70° C. for 2 hours. The mixture was diluted with dichloromethane (4 ml) and filtered down a short column of silica (Varian Bond-sluts S1 silica) eluting with a gradient of 0:100 (v/v) to 100:0 (v/v) methanol/dichloromethane. The appropriate organic fractions were combined, washed with saturated aqueous sodium carbonate (3×30 ml), dried ($Na_2CO_3$) and evaporated to give 3-[2-(4-[2-methyl-tetrazol-5-yl]phenyl) ethynyl]-3-hydroxyquinuclidine (260 mg) as a solid, m.p. 228°–230° C.; microanalysis, found: C, 65.9; H, 6.1; N, 22.2%; $C_{17}H_{19}N_5O$ requires: C, 66.0; H, 6.2; N, 22.6%; NMR: 1.2–1.4(1H,m), 1.5–1.7(1H,m), 1.8–2.0(3H,m), 2.7 (4H,m), 2.8–3.2(2H,m), 4.4(3H,s), 5.6(1H,s), 7.6(2H,m), 8.05(2H,m); m/z 310(M+H).

The 2-methyl-5-(4-bromophenyl)tetrazole used as starting material was obtained as described in Perkin, Trans II, (1984), 721 (also R. N. Butler et al, J. Chem. Res. 5, (1981) 174).

EXAMPLE 50

Illustrative pharmaceutical dosage forms suitable for presenting the compounds of the invention for therapeutic or prophylactic use include the following tablet and capsule formulations, which may be obtained by conventional procedures well known in the art of pharmacy and are suitable for therapeutic or prophylactic use in humans:

| (a) Tablet I | mg/tablet |
|---|---|
| Compound Z* | 1.0 |
| Lactose Ph. Eur. | 93.25 |
| Croscarmellose sodium | 4.0 |
| Maize starch paste (5% w/v aqueous paste) | 0.75 |
| Magnesium stearate | 1.0 |
| (b) Tablet II | mg/tablet |
| Compound Z* | 50 |
| Lactose Ph. Eur | 223.75 |
| Croscarmellose sodium | 6.0 |
| Maize starch | 15.0 |
| Polyvinylpyrrolidone (5% w/v aqueous paste) | 2.25 |
| Magnesium stearate | 3.0 |
| (c) Tablet III | mg/tablet |
| Compound Z* | 100 |
| Lactose Ph. Eur. | 182.75 |
| Croscarmellose sodium | 12.0 |
| Maize starch paste (5% w/v aqueous paste) | 2.25 |
| Magnesium stearate | 3.0 |
| (d) Capsule | mg/capsule |
| Compound Z* | 10 |
| Lactose Ph. Eur. | 488.5 |
| Magnesium stearate | 1.5 |

Note
*The active ingredient Compound Z is a compound of formula I, or a salt thereof, for example a compound of formula I described in any of the preceding Examples.

The tablet compostions (a)–(c) may be enteric coated by conventional means, for example, with cellulose acetate phthalate

SCHEME 1

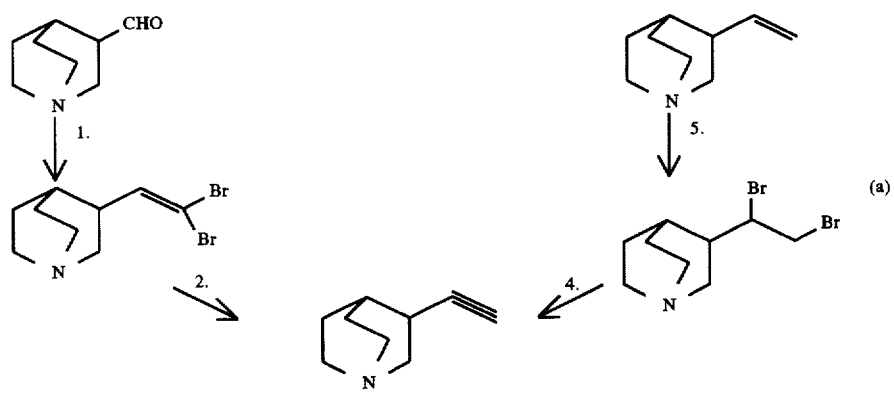

1. CBr$_4$/PPh$_3$/Zn, CH$_2$Cl$_2$, ROOM TEMPERATURE
2. (a) n.BuLi (2 equiv), THF, −60° C., ARGON ATMOSPHERE (b) H$_2$O
3. Br$_2$/H$_2$O
4. t.BuOK, t-BuOH, REFLUX

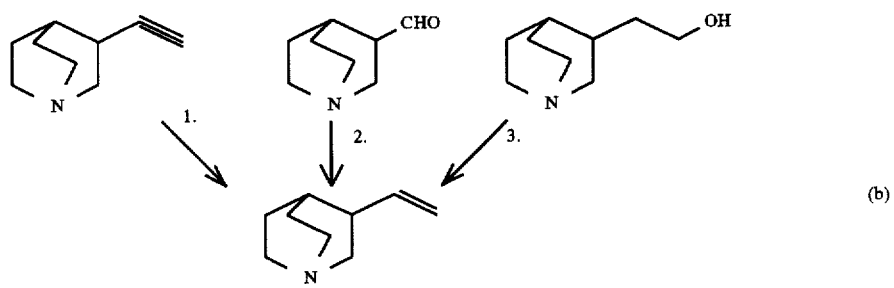

1. H$_2$/Pd. —CaCO$_3$, EtOH
2. Ph$_3$⊕PCH$_3$Br⊖, KOBu$^t$, THF
3. PHTHALIC ANHYDRIDE, BENZENE SULPHONIC ACID, 280° C.

SCHEME 2

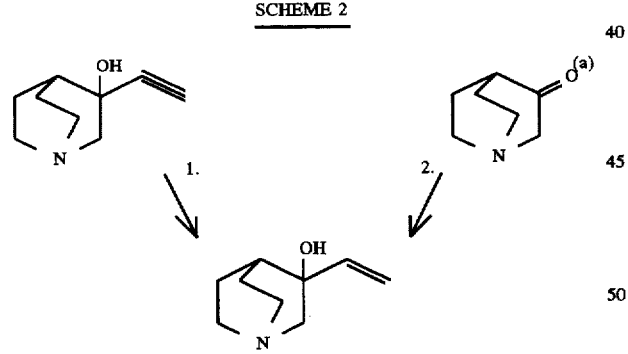

1. H$_2$/Pd—CaCO$_3$, ETOH
2. (a) H$_2$C=CHMgBr, THF, 20–25° C. (b) NH$_4$Cl solution

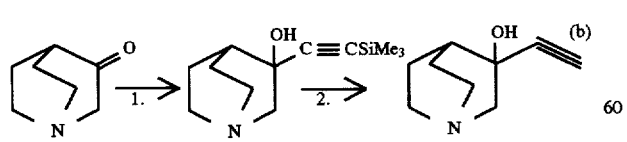

1. Me$_3$Si—C≡C—Li, THF, −70° C. to −75° C., ARGON ATMOSPHERE
2. K$_2$CO$_3$, MeOH, 20–25° C.

CHEMICAL FORMULAE

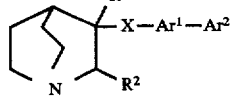  (I)

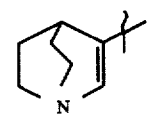  (Ia)

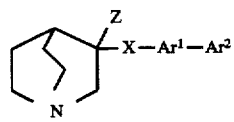  (II)

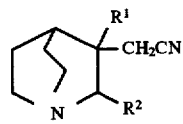  (III)

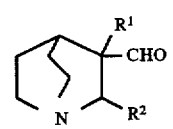  (IV)

-continued
CHEMICAL FORMULAE

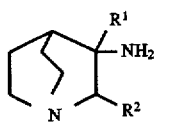 (V)

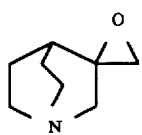 (VI)

 (VII)

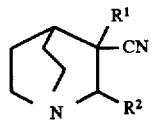 (VIII)

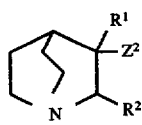 (IX)

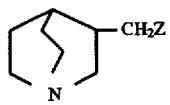 (X)

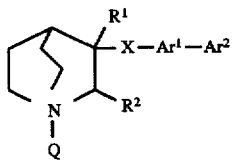 (XI)

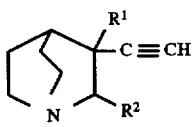 (XII)

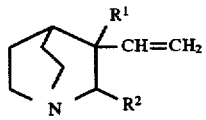 (XIII)

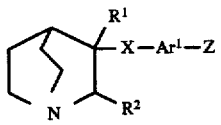 (XIV)

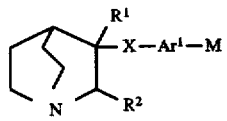 (XV)

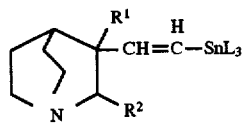 (XVI)

-continued
CHEMICAL FORMULAE

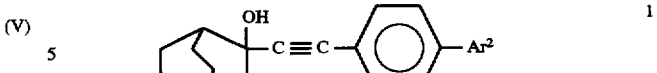 1

 2

We claim:
1. A compound of formula I

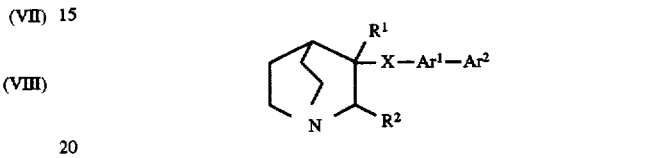

wherein:
$R^1$ is hydroxy;
$R^2$ is hydrogen;
X is selected from —CH$_2$CH$_2$—, —CH=CH—, —C≡C—, —CH$_2$O—, —CH$_2$NH—, —CH$_2$CO—, —COCH$_2$— and —CH$_2$S—;
$Ar^1$ is a phenylene moiety;
$Ar^2$ is a heteroaryl moiety selected from a monocyclic 6-membered heteroaryl ring containing one heteroatom selected from nitrogen, oxygen and sulphur, and a monocyclic 5-membered heteroaryl ring containing one, two, three or four heteroatoms selected from nitrogen, oxygen and sulphur; and
wherein one or both of $Ar^1$ and $Ar^2$ may optionally bear one or more substituents independently selected from halogen, hydroxy, amino, nitro, cyano, carboxy, carbamoyl, (1–6C)alkyl, (2–6C)alkenyl, (2–6C)alkynyl, (1–6C)alkoxy, (1–6C)alkylamino, di-[(1–6C)alkyl]amino, N-[(1–6C)alkyl]carbamoyl, N,N-di-[(1–6C)alkyl]carbamoyl, (1–6C)alkoxycarbonyl, (1–6C)alkylthio, (1–6C)alkylsulphinyl, (1–6C)alkylsulphonyl, halogeno-(1–6C)alkyl, carboxy(1–6C)alkyl and (1–6C)alkanoylamino.

2. A compound as claimed in claim 1 wherein $Ar^2$ is selected from furyl, pyrrolyl, thienyl, pyridyl, imidazolyl, oxazolyl, isooxazolyl, thiazolyl, isothiazolyl, oxadiazolyl, triazolyl, pyrazolyl and thiadiazolyl.

3. A compound as claimed in claim 1 wherein X is selected from —CH$_2$CH$_2$—, —CH=CH—, —C≡C—, —CH$_2$O—, —CH$_2$NH— or —CH$_2$S—.

4. A compound as claimed in claim 1 wherein X is selected from —CH$_2$CH$_2$—, —CH=CH—, —C≡C— and —CH$_2$O—.

5. A compound as claimed in claim 1 wherein $Ar^1$ is 1,4-phenylene.

6. A compound as claimed in claim 5 wherein $Ar^2$ is an oxadiazolyl moiety.

7. A compound as claimed in claim 1 which is selected from:
3-[2-(4-[3-pyridyl]phenyl)ethenyl]-3-hydroxyquinuclidine;
3-[2-(4-(5-methyl-1,2,4-oxazdiazol-3-yl)phenylethynyl]-3-hydroxyquinuclidine;
3-[2-(4-(3-methyl-1,2,4-oxazdiazol-5-yl)phenylethynyl]-3-hydroxyquinuclidine;
3-[2-(4-[3-methyl-1,2,4-thiadiazol-5-yl]phenyl)ethynyl]-3-hydroxy quinuclidine;

3-[2-(4-(2-ethyl-1,3,4-oxadiozol-5-yl)phenyl)ethynyl]-3-hydroxy quinuclidine;

(+)-3-[2-(4-[5-methyl-1,2,4-oxadiazol-3-yl]phenyl)ethynyl]-3-hydroxy quinuclidine;

(−)-3-[2-(4-[5-methyl-1,2,4-oxadiazol-3-yl]phenyl)ethynyl]-3-hydroxy quinuclidine;

3-[2-(E)-(4-[5-ethyl-1,2,4-oxadiazol-3-yl]phenyl)ethenyl]-3-hydroxy quinuclidine;

3-[2-(2-allyl-4-(5-methyl-1,2,4-oxadiazol-5-yl)ethynyl]-3-hydroxyquinuclidine;

3-[2-(4-(5-methyl-1,2,4-oxadiazol-3-yl)phenyl)ethenyl]-3-hydroxyquinuclidine;

3-[2-(4-(2-methyl-tetrazol-5-yl)phenyl)ethynyl]-3-hydroxyquinuclidine;

and pharmaceutically acceptable salts thereof.

8. A process for preparing a compound as claimed in claim 1 wherein:

(p) for those compounds in which X is —C≡C— and $R^1$ is hydrogen or hydroxy and $R^2$ is hydrogen, reacting a compound of formula XII in which $R^1$ is hydrogen or hydroxy and $R^2$ is hydrogen with a compound of formula $Ar^2$—$Ar^1$—Z in which Z is a leaving group in the presence of a catalyst;

and whereafter when a pharmaceutically acceptable salt is required reacting the compound of formula I with an acid which affords a physiologically acceptable anion or a base which affords a physiologically acceptable cation.

9. A pharmaceutical composition comprising a compound of formula I, or a pharmaceutically-acceptable salt thereof, as claimed in claim 1 together with a pharmaceutically acceptable diluent or carrier.

10. A method of inhibiting cholesterol biosynthesis in a warm blooded animal, such as man, which method comprises administering an effective amount of a compound of formula I, or a pharmaceutically acceptable salt thereof, as defined in claim 1 to said animal.

11. A method of treating a disease or medical condition selected from hypercholesterolemia and atherosclerosis comprising administering an effective amount of a compound of formula I, or a pharmaceutically acceptable salt thereof, as defined in claim 1 to a warm blooded animal, such as man.

12. A compound as claimed in claim 5 wherein one or both of $Ar^1$ and $Ar^2$ may optionally bear one or more substituents selected from halogen, hydroxy, nitro, (1–6C)alkyl, (2–6C)alkenyl, (1–6C)alkoxy, (1–6C)alkylthio, (1–6C)alkylsulphinyl, (1–6C)alkoxycarbonyl, (1–6C)alkylsulphonyl, (1–6C)alkanoylamino and halogen(1–6C)alkyl.

* * * * *